United States Patent [19]

Romano

[11] Patent Number: 5,002,546
[45] Date of Patent: Mar. 26, 1991

[54] CURVED BORE DRILLING APPARATUS

[76] Inventor: Jack W. Romano, 412 NE. 165th, Apt. #13, Seattle, Wash. 98155

[21] Appl. No.: 510,743

[22] Filed: Apr. 18, 1990

Related U.S. Application Data

[63] Continuation-in-part of Ser. No. 196,319, May 20, 1988, Pat. No. 4,941,466, which is a continuation-in-part of Ser. No. 37,697, Apr. 13, 1987, abandoned.

[51] Int. Cl.$^5$ ............................................. A61B 17/16
[52] U.S. Cl. .......................................... 606/80; 606/96; 606/180; 408/127; 408/146; 408/187
[58] Field of Search ............... 606/80, 96, 103, 180; 175/61.75, 73, 74, 75; 408/1 R, 127, 136, 146, 147, 187, 188; 81/177.6

[56] References Cited

U.S. PATENT DOCUMENTS

| | | | |
|---|---|---|---|
| 1,223,938 | 4/1917 | Close | 82/1.5 |
| 1,698,952 | 1/1929 | Hoover | 173/50 |
| 1,822,330 | 9/1931 | Ainsle | 606/145 |
| 2,291,413 | 4/1942 | Siebrandt | 128/83 |
| 2,666,430 | 1/1954 | Gispert | 128/83 |
| 2,747,384 | 5/1956 | Beam | 464/52 |
| 2,905,178 | 9/1959 | Hilzinger | 128/303 R |
| 3,554,192 | 1/1971 | Isberner | 128/83 |
| 3,628,522 | 12/1971 | Kate | 128/751 |
| 3,697,188 | 10/1972 | Pope | 408/230 |
| 3,815,605 | 6/1974 | Schmidt et al. | 128/305 |
| 4,257,411 | 3/1981 | Cho | 606/96 |
| 4,265,231 | 5/1981 | Scheller, Jr. et al. | 606/80 |
| 4,312,337 | 1/1982 | Donohue | 606/80 |
| 4,345,601 | 9/1982 | Fukuda | 606/147 |
| 4,421,112 | 12/1983 | Mains et al. | 606/88 |
| 4,541,423 | 9/1985 | Barber | 606/80 |
| 4,590,929 | 5/1986 | Klein | 606/74 |
| 4,622,960 | 11/1986 | Tam | 606/103 |

FOREIGN PATENT DOCUMENTS 1168222 3/1983 U.S.S.R. .

Primary Examiner—Robert A. Hafer
Assistant Examiner—Kevin G. Rooney
Attorney, Agent, or Firm—Cassidy, Vance & Tarleton

[57] ABSTRACT

Curved bore drilling apparatus and methods having a remotely actuated, pivotal rocker arm and cantilevered, curved guide means which guide and advance a cutting means through a predetermined curved path to drill one or more curved bores within a solid material.

33 Claims, 12 Drawing Sheets

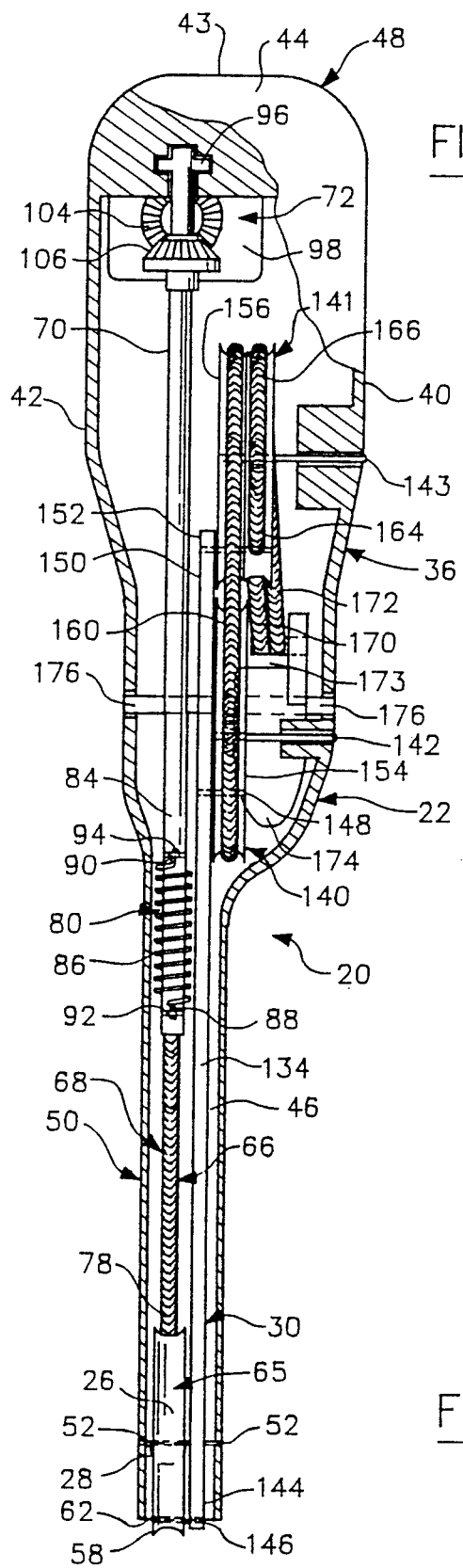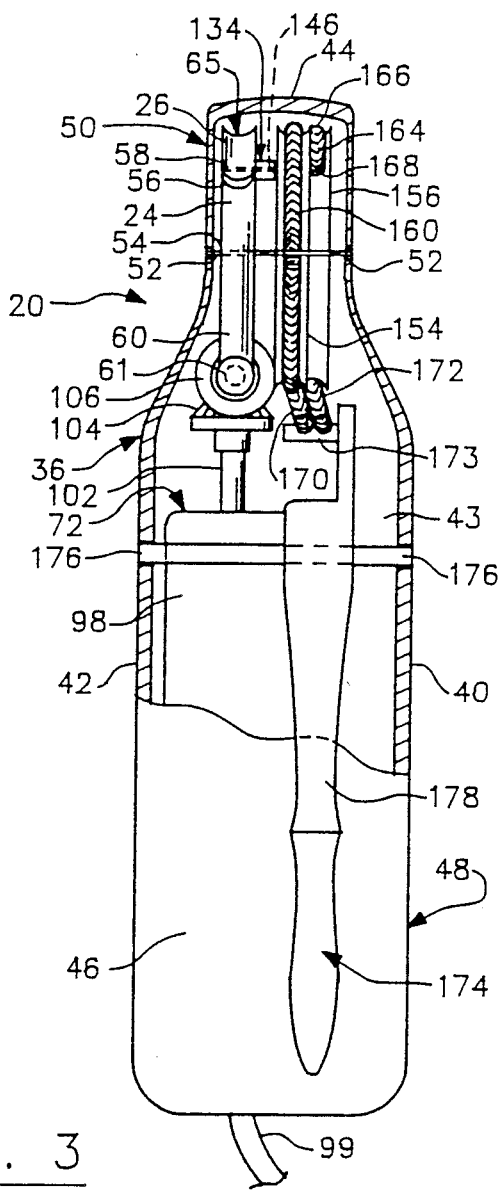
FIG. 2
FIG. 3

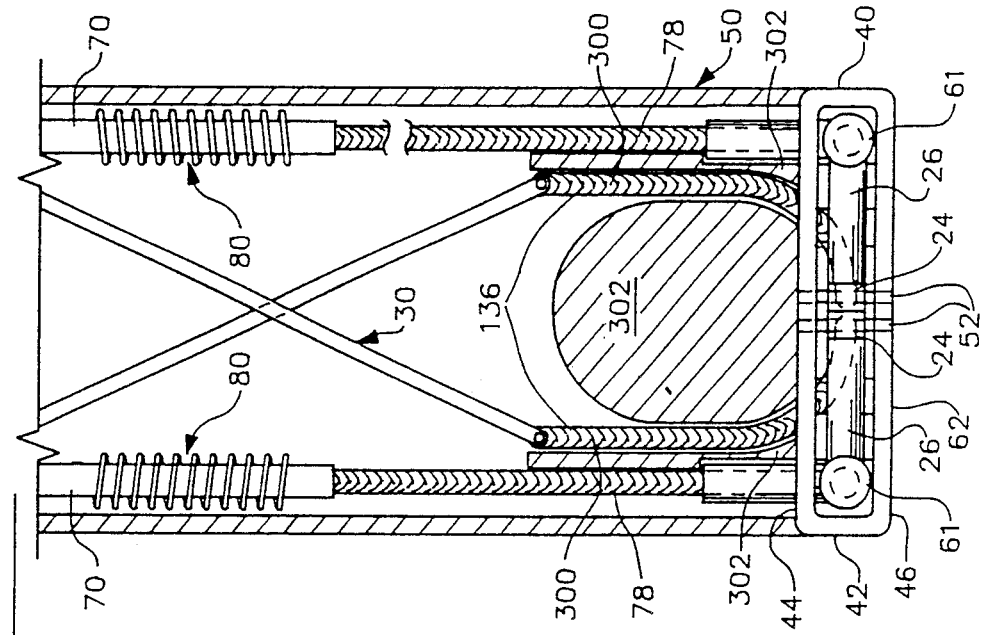
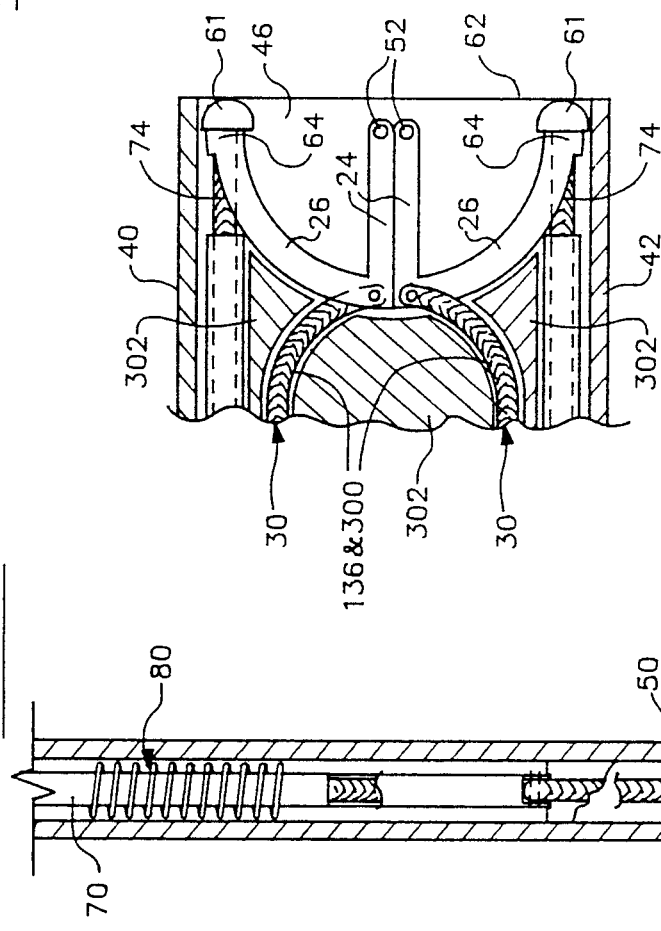
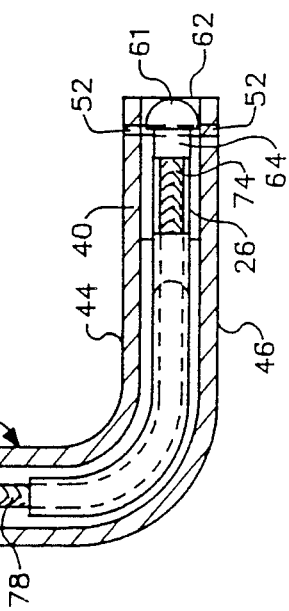

CURVED BORE DRILLING APPARATUS

CROSS REFERENCE TO RELATED APPLICATION

This is a continuation-in-part of a commonly owned, copending patent application, titled "CURVED BORE DRILLING METHOD AND APPARATUS", Ser. No. 07/196,319, which was filed in the United States Patent and Trademark Office on May 20, 1988 and is now U.S. Pat. No. 4,941,466. That patent application was a continuation-in-part of an earlier, now abandoned patent application, titled "CURVED BORE DRILLING METHOD AND APPARATUS", Ser. No. 07/037,697, which was filed in the United States Patent and Trademark Office on Apr. 13, 1987. The Specifications and Drawings of these earlier patent applications are incorporated herein by reference.

COPYRIGHT NOTICE

©Copyright 1990, James R. Vance. All Rights Reserved

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyrights whatsoever.

1. Technical Field

This invention relates to apparatus and methods for forming or drilling one or more curved bores or holes into a solid material; and, more particularly, to drilling apparatus having a remotely actuated, pivotal rocker arm and curved guide means which guide and advance a cutting means through a predetermined curved path within a solid material.

2. Background Art

Many industries, including the health profession, often desire to produce curved bores. Cannulas, lumens, ducts, and other types of tubular and curved conduits are each needed for particular purposes. Machinery often need such conduits to transport fuel, coolants, cutting fluids, gases, products, and/or by-products. Similarly, curved conduits are often needed within the plumbing, electrical, and heating industries to transport fluid, wiring, and heating around restricted corners.

Heretofore, machining for curved conduits has been near impossible. Curved bores within solid objects have been particularly difficult. A plurality of straight bores may be used at various angles in an attempt to round difficult corners. Other options are to form a precast mold having a removable curved plug for a core, or to prepare multiple piece vacuum or injection molds. Such tooling techniques are time-consuming and expensive.

The need for curved bores also exists within the field of orthopedic surgery. For example, it is often desirable to secure a suture or a wire to a bone to: secure a tissue, such as ligament; immobilize adjacent bone structures; and/or reduce a fracture. Traditional practice is to make two independent straight bores at intersecting angles at some angle less than 180° within the bone structure. A curved needle is then gradually forced through the bone from one bore hole to the other. This practice is highly susceptible to operational error. Such a procedure is also very time consuming if the bore holes do not intersect or if the permitted working area is restricted.

In some instances severe damage can be caused to the surrounding bone structure and soft tissue. By its very nature, this procedure removes more bone than is desireable. It is also not uncommon to break a needle within hard bone structure by using too much force in attempting to force a curved needle through two straight holes, thus, necessitating additional time and inconvenience to retrieve the broken needle fragments. This greatly increases the expense to perform the operation. Additional anesthesia is required which also increases the risk associated with the operation.

The following surgical devices were created in an attempt to overcome such difficulties.

Scheller, Jr, et al. (U.S. Pat. No. 4,265,231; issued May 5, 1981) lists a number of specific examples of such operations wherein a curved bore is advantageous and describes one known method and apparatus for forming curved bores. The Scheller device is an example of the use of a flexible drill containing cannula of a predetermined curvature which may be hand-manipulated through its curved path within bone.

As may be appreciated, the manipulation of such a cannula requires a considerable amount of space and it is thus of limited utility where access is limited. The space requirement for operation of the instrument also necessitates a considerably larger skin incision. Not only does the manipulation of the hand held cannula and drive motor require additional space, but the cumbersome size and shape of the cannula itself severely limits the utility of the Scheller device.

Other examples of the use of a rigid curved cannula are illustrated in Barber (U.S. Pat. No. 2,541,423; issued Sept. 17, 1985) and in Donohue (U.S. Pat. No. 4,312,337; issued Jan. 26, 1982). These devices suffer from the same limitations discussed above with respect to the Scheller method and apparatus.

In each of the cited patents, the cannula is used to push, pull or advance the drill shaft through a curved path determined by the operator's manipulation of the entire instrument. Allowance must be made for the shape of the preformed cannula.

The primary problems with the apparatus and methods of the prior art are: the time consuming nature of the procedures; the inability to operate in a restricted area; and the possibility of severe damage to bone and/or to surrounding tissue. The results of these drawbacks may have far reaching effect in terms of the cost of the surgery, the degree of scarring, and the recovery and rehabilitation time required, as well as increased anesthesia risks.

Furthermore, modern day trends of reducing incision size and decreasing tissue violation do not lend themselves well to the sometimes crude and inexact methods currently in practice, or described in any of the cited patent. For example, in the practice of arthroscopic surgery an instrument is inserted into a joint cavity through an extremely small puncture incision which is only large enough to allow entrance of the instrument. The cavity and manipulation of the instrument is observed by means of a scope device inserted through a second near size incision. Curved bone drilling under these conditions is presently nonexistent, and would be extremely difficult if not impossible with known bone drilling devices.

The inventor believes that the listed patents and known prior art taken alone or in combination neither anticipate nor render obvious the present invention. These citations do not constitute an admission that such disclosures are relevant or material to the present claims. Rather, these citations relate only to the general field of the disclosure and are cited as constituting the closest art of which the inventor is aware.

DISCLOSURE OF INVENTION

The present invention may be used within a wide variety of industries wherein simple, easy, inexpensive apparatus and methods are desired to form one or more curved bores within a solid material. More particularly, this invention provides apparatus and methods for using a remotely actuated, pivotal rocker arm and curved guide means to guide and advance a cutting means through a predetermined curved path within a solid material.

The claimed apparatus and methods further contemplate use of traditional and/or nontraditional machining processes, including mechanical, electrochemical, and thermal processes. Such cutting means may be remotely actuated by a wide variety of actuation means. Furthermore, the present invention allows the cutting means to have a wide range of orientations with respect to the bored surface.

The present invention is a compact, functional, efficient, reliable, reusable, durable, rugged, easily constructed, inexpensive and economical to manufacture apparatus that requires minimal manipulation and is simple to use. The present invention not only increases the speed and simplifies the procedure to form curved bores, it also provides an inexpensive, unobtrusive drilling apparatus which requires less access room for operation and does not damage adjacent material. During use, it is unnecessary to alter the angle of approach of a support structure, such as the housing of the apparatus, with respect to the material to be drilled. This enables curved bores to be formed within material, such as bone, through a very small incision which allows access to a deep bone structure, without damaging adjacent bone structure or tissue. The present invention also overcomes all of the previously mentioned disadvantages.

To achieve these general and specific objects the present invention comprises: a support structure; a rocker arm; curved guide means; cutting means; and actuation means.

The support structure may take any form which appropriately orients the apparatus with respect to the material to be drilled. The support structure may comprise an independent, dedicated support stand, an arm extending from a larger machine or structure, a handheld housing unit, or similar structure which meets the particular needs of the user.

The rocker arm is pivotally secured to the support structure at a fixed pivot point and rotates about an axis of rotation. This pivot point is extremely important to the present invention. In essence, the movement of the guiding means and cutting means, which will be described further below, is dependent upon their rotation about this fixed pivot point. Likewise, the bore to be formed within the material will also depend upon a predetermined curved path defined by a rotation about this fixed pivot point.

Once a fixed spacial relationship is achieved between the drilling apparatus and the material to be drilled, rotation of the rocker arm, curved guide means, and cuttings means permits a curved bore to be formed within the material.

The pivot point may comprise a cylindrical pivot pin which pivotally secures the rocker arm to the support structure. The rocker arm defines a rotating link or crank which rotates and/or oscillates about the fixed pivot point. The rocker arm has a first end located near the fixed pivot point and has a second end extending radially outward from the fixed pivot point.

The curved guide means defines an arcuate tube or channel having a first end rigidly attached to the second end of the rocker arm. The curved guide means has an extended second end which cantilevers outwardly from the rocker arm. The curved guide means generally lies within an arc defined by the rotational path of the second end of the rocker arm as the rocker arm is rotated about its fixed pivot point. The length of the rocker arm and the length and cross-sectional area of the curved guide means are dependent upon the desired curve, length, and cross-sectional area of the curved bore to be formed.

The pivot point is located near a protrusion or edge of the support structure in such a manner that when the rocker arm is pivoted or rotated, the second end of the curved guide means extends away from the support structure passing through a predetermined curved path. Thus, if a material is juxtaposed near the pivot point and support structure, rotation or pivotal movement of the rocker arm will urge the second end of the curved guide means toward the material.

The forward, cantilevered, or extended second end of the curved guide means is provided with means for securing the cutting means thereto. Such securing means may comprise a collar, bearing, a bushing, or other structure to hold and retain the cutting means in place.

The cutting means may comprise any apparatus or method which is capable of cutting the material within the confines of a curved bore. Traditional or nontraditional machining processes may be used, including mechanical, electrochemical, and thermal processes. In one embodiment, the inventor prefers to use a electric discharge machining (EDM) process. In another embodiment, a rotary cutting means is used.

As stated above, the curved guide means may comprise an arcuate tube or channel. Whether the curved guide means is a tube or channel largely depends upon the cutting and machining process used.

Some processes allow a portion of the cutting means to be placed and contained within a tubular curved guide means. An appropriately powered pivotal connection is then made at the fixed pivot point of the rocker arm to transfer power from a remote power source to a leading, boring tip or cutting head secured near the second end of the curved guide means. Electric discharge machining (EDM) allows for such a connection.

Alternatively, the cutting means may require the use of a flexible shaft which is directly connected to a remote power source. To accommodate such a connection, the curved guide means is provided with an outwardly extending receiving channel which is used to guide, receive, and retain the flexible shaft of the cutting means. For example, some processes require rotational power obtained from a remote rotational power source to be transmitted through a flexible drill shaft to rotate a leading cutting head. To use such a cutting means, the second end of the curved guide means is provided with a securing means which permits rotation of the secured cutting head. The curved guide means is also provided with an exterior channel which is designed to guide, receive and retain the rotatable, flexible shaft. As the rocker arm is pivoted, the curved guide means and cutting head are advanced toward the material. The channel of the curved guide means receives and retains the flexible shaft as the cutting head and curved guide means advance toward and through the material.

Thus, when the rocker arm is pivoted, the curved guide means guides and advances the cutting means away from the support structure to bore a hole along a predetermined curved path within the material.

After the bore has been created, the motion of the rocker arm is reversed and the curved guide means and cutting means are removed from within the material. The insertion and retraction of the curved guide means and cutting means into and from the material is defined by the oscillation of the rocker arm.

The pivotal rocker arm, curved guide means, and cutting means may be remotely actuated by a wide variety of actuation means. The actuation means urges the rocker arm to rotate, which in turn urges the curved guide means and cutting means to advance or retract through the predetermined curved path.

Several different actuation means are described in detail in the following text. The simplest actuation means, however, is where the first end of the rocker arm is rigidly attached to one end of an elongated pivot pin. The pivot pin is rotatably secured to the support structure, and a crank or lever is rigidly attached to a second end of the pivot pin. Rotation of the crank causes the pivot pin to rotate, which causes the rocker arm to rotate, which in turn causes the curved guide means and cutting means to advance or retract through the predetermined curved path. A spring may also be used to urge rotation of the rocker arm.

Alternatively, a connecting rod or push/pull linkage may be pivotally secured to either the rocker arm or to the curved guide means. Preferably, the connecting rod is secured at a juncture or intersection of the rocker arm and of the curved guide means. Appropriate movement of the connecting rod will cause the rocker arm, curved guide means, and cutting means to advance or retract through the predetermined curved path.

In a first embodiment of the present invention the actuation means comprises a double parallel-crank mechanism. The rocker arm, and two different crank systems are rotationally secured to the support structure. A single connecting rod is then connected to the rocker arm and to each of the two crank systems. A first end of the connecting rod is pivotally secured to the rocker arm. The first crank system is pivotally connected to the connecting rod at an intermediate location along the length of the connecting rod. A second end of the connecting rod is pivotally connected to the second crank system. In essence, the support structure, rocker arm, connecting rod, first crank system and second crank system form a plane parallelogram. Means for rotating the first and second crank systems are also provided. For example, one or more tension cords, chains, cables, or the like may be used to rotate the first and/or second crank systems. Similarly, a spring may be used to urge one or more crank systems toward rotation or to retract the crank systems from an earlier rotation. The tension cords may then be connected to an easily controlled lever, trigger, switch, or the like.

The first and/or second crank systems may one or more pulleys incorporated therein. Such pulleys share the same axis of rotation as their corresponding crank system. The above mentioned tension cord may be passed around one or more of the pulleys to provide smooth, easy actuation and rotation of the plane parallelogram and attached curved guide means and cutting head.

In a second embodiment the pulleys and tension cords are replaced with a rack and pinion system.

In a further embodiment of the actuation means a crossed-crank mechanism may be used.

In still further embodiments, multiple rocker arms, curved guide means, cutting means, and actuation means may be used in unison or within a single apparatus.

The present invention allows the cutting means to have a wide range of orientations with respect to the bored surface. This is accomplished by controlling the path and angle of rotation of the curved guide means and cutting means, and by placing the curved guide means and cutting means at various angles with respect to the remaining elements of the apparatus and/or with respect to the bored material.

Due to pressure to reduce medical costs, greater emphasis is made to increase efficiency and reduce the time required to perform various procedures. Any reduction in time, and increase in accuracy and efficiency is therefor of great significance. Further, the modern trend is toward procedures which reduce incision size and tissue violation. The latter trend is demanded not only for cost reduction and shortened recovery time, but also to reduce pain, scarring, rehabilitation time, anesthesia risk, required pain medication, and wage loss during recovery.

The present invention greatly simplifies conventional and arthroscopic surgery, and provides an apparatus and methods to produce a curved bore with great accuracy and with minimum damage to adjacent bone and tissue within an extremely limited incision. For example, curved bores may now be formed in shoulder joints at difficult locations using safe, conventional puncture sites. When used, this invention allows the attachment of filament to bone in an exact and efficient manner, saving time and cost, and permitting the operation to be performed within very small, deep incision, heretofore impossible with prior art devices. As a consequence of it efficiency, the present invention also decreases postoperative therapy and expense.

These and other objects and advantages of the present invention will become more readily apparent upon reading the following disclosure and referring to the attached drawings.

BRIEF DESCRIPTION OF DRAWINGS

FIG. 2 is a plan view of the first embodiment shown in FIG. 1, wherein a portion of an upper wall of the housing is removed to illustrate the interrelationship between the interior rocker arm, curved guide means, cutting means, and actuation means.

FIG. 3 is a front-elevational view of the first embodiment shown in FIGS. 1 and 2 with a portion of the front and upper walls of the housing removed.

FIG. 7 is a partial side-elevational view of the support structure, rocker arm, curved guide means having an external receiving channel, and cutting means having a flexible shaft which is directly connected to a cutting head.

FIG. 8 is a partial side-elevational view of an alternative embodiment, wherein the support structure, rocker arm, and curved guide means are tubular in construction and communicate with one another to allow the cutting means to be contained therein.

FIG. 17 is a partial, cross-sectional, side-elevational view of a seventh embodiment of the invention shown in FIGS. 18 and 19, wherein the rigid drive shafts rest within a plane which is generally perpendicular to the plane within which the multiple rocker arms, curved guide means, and cutting means rotate.

FIG. 18 is a partial, plan view of the seventh embodiment shown in FIGS. 17 and 19.

FIG. 19 is a partial, cross-sectional, front-elevational view of the seventh embodiment shown in FIGS. 17 and 19.

Figure 1:
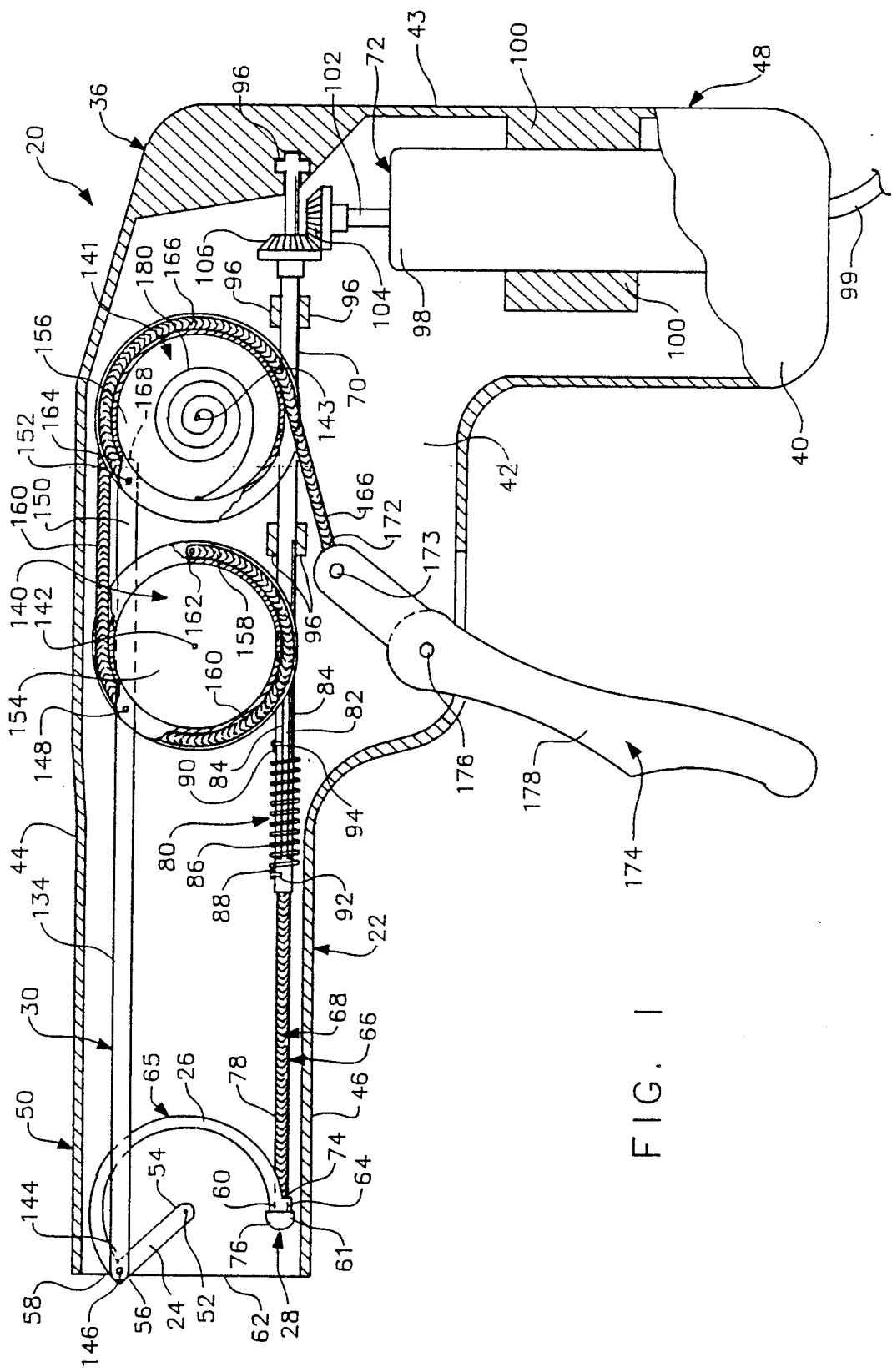
FIG. 1 is a side-elevational view of a first embodiment of the drilling apparatus as taught herein with a portion of a left wall of a support structure housing removed to illustrate an interior rocker arm, curved guide means, cutting means, and actuation means.

One should understand that the drawings are not necessarily to scale and the elements are sometimes illustrated by graphic symbols, phantom lines, diagrammatic representations, and fragmentary views. In certain instances, the inventor may have omitted details which are not necessary for an understanding of the present invention or which render other details difficult to perceive.

BEST MODE FOR CARRYING OUT THE INVENTION

Referring to the drawings, wherein like numerals indicate like parts, a curved bore drilling apparatus 20 of the present invention comprises: a support structure 22; a rocker arm 24; curved guide means 26; cutting means 28; and actuation means 30.

SUPPORT STRUCTURE

Support structure 22 may take any form which appropriately orients drilling apparatus 20 with respect to a material 31 to be drilled. For example, support structure 22 may comprise an extension or arm of a separate larger machine or structure (not shown).

Figure 9:
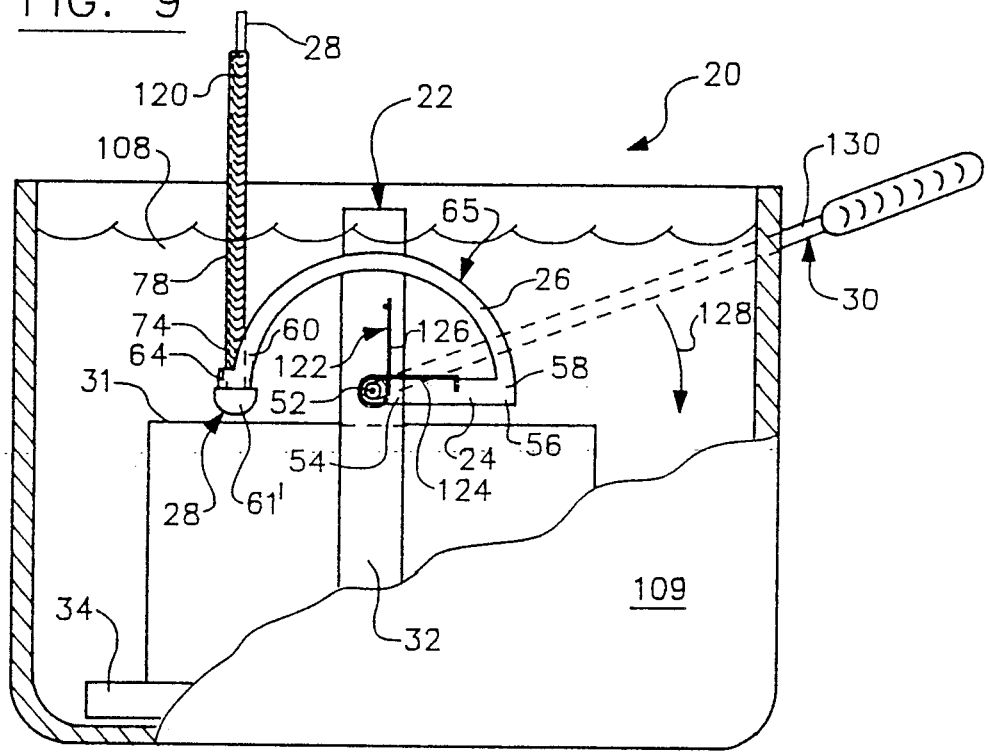
FIG. 9 is a schematic, partially sectioned, sideelevational view of a forth embodiment of the present invention which incorporates the use of an electric discharge machining (EDM) process.
Figure 10:
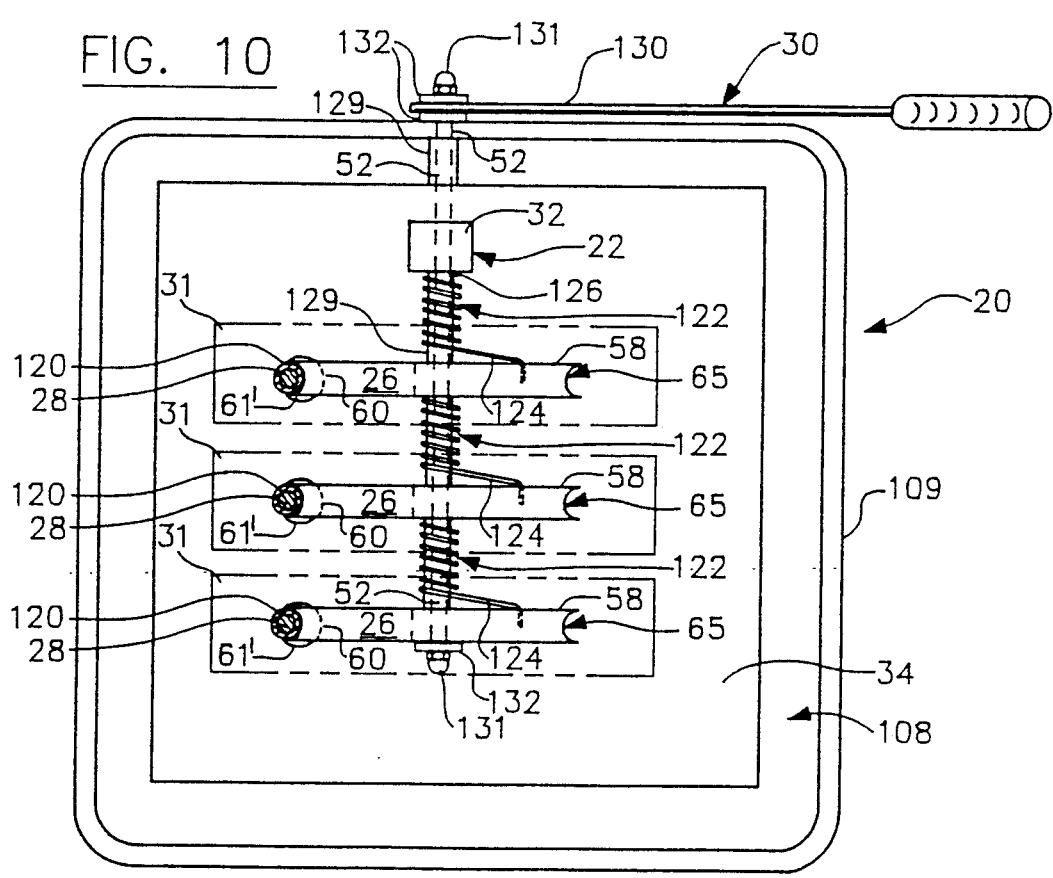
FIG. 10 is a schematic, plan view of the forth embodiment shown in FIG. 9.

Support structure 22 may also be an independent support stand specifically dedicated to supporting the remaining elements of drilling apparatus 20. As shown in FIGS. 9 and 10, support structure 22 may simply comprise an upright post 32 which is secured to a horizontal base 34. Upright post 32 or horizontal base 34 may serve other purposes, such as holding the material 31 to be drilled.

In the preferred embodiment, support structure 22 comprises a housing 36 which defines the parameters of an enclosure 38 located therein. Housing 36 supports, protects, and contains rocker arm 24, curved guide means 26, cutting means 28, and actuation means 28. Housing 36 has an opening into enclosure 38. The opening is located near rocker arm 24, curved guide means 26, and cutting means 28.

For easy use, housing 36 may be a hand-held unit of any size and shape which meets the particular needs of a user.

For use in arthroscopic surgery, housing 36 has a pistol shape which is easily held. As seen in FIG. 1, housing 36 may comprise: a left wall 40, a right wall 42, a rear wall 43, an upper wall 44, and a lower wall 46, which generally define a handle portion 48 and a neck portion 50 of housing 36. Typically, neck portion 40 of housing 36 is extremely thin and narrow to allow placement of rocker arm 24, curved guide means 26, and cutting means 28 deep within a small, narrow incision (not shown). However, to better illustrate the interrelationship between housing 36, neck portion 40, rocker arm 24, curved guide means 26, cutting means 28, and actuation means 30, the size and dimensions of such elements have been substantially enlarged within FIGS. 1-6 and 11-20.

ROCKER ARM

Rocker arm 24 is pivotally secured to housing 36 at a fixed pivot point which defines its axis of rotation. As shown in FIG. 1, the fixed pivot point may comprise a pivot pin 52 which pivotally secures rocker arm 24 to housing 36. Pivot pin 52 may be secured to either left wall 40 or to right wall 42. In the preferred embodiment, pivot pin 52 is secured to both left wall 40 and to right wall 42 and spans the distance within enclosure 38 between such walls.

Rocker arm 24 defines a rotating link or crank which rotates and/or oscillates about pivot pin 52. Rocker arm 24 has a first end 54 located near pivot pin 52 and has a second end 56 which extends radially outward from pivot pin 52.

CURVED GUIDE MEANS

Curved guide means 26 defines an arcuate tube and/or channel having a first end 58 which is rigidly attached to or integrated with second end 56 of rocker arm 24. Rocker arm 24 and curved guide means 26 may be attached together by any appropriate means such as by adhesion, bolting, welding, or the like. In the preferred embodiment, rocker arm 24 and curved guide means 26 are formed from a single piece of material. Such single piece of material is then appropriately bent to form second end 56 of rocker arm 24 and first end 58 of curved guide means 26.

Curved guide means 26 also has an extended second end 60 which cantilevers outwardly from second end 56 of rocker arm 24. Curved guide means 26 generally lies within an arc that is defined by the rotational path of second end 56 of rocker arm 24 as rocker arm 24 is pivoted and/or rotated about pivot pin 52.

The angle of curvature, cross-sectional area, and depth of the curved bore to be formed, are dependent upon various factors including: the longitudinal length of rocker arm 24; the curved length of curved guide means 26; the crosssectional area of curved guide means 26; the angle of rotation of rocker arm 24; and the cross-sectional area of a cutting portion 61 of cutting means 28. Such lengths, crosssectional areas, and angles of rotation will in turn be dependent upon: the type of material 31 to be drilled; accessibility to that particular portion of material 31; the type of cutting means 28 used; and other factors commonly considered in drilling processes.

To enable drilling apparatus 20 to drill a curved bore having a large angle of curvature or rotation, pivot pin 52 is located as near as possible or as is desirable to a protrusion or edge 62 of housing 36. Rocker arm 24 is secured to housing 36 in such a manner that when rocker arm 24 is pivoted or rotated, second end 60 of curved guide means 26 extends and cantilevers away from housing 36, passing through a predetermined curved path. Thus, if material 31 is juxtaposed near edge 62 of housing 36, rotation or pivotal movement of rocker arm 24 will urge second end 60 of curved guide means 26 toward material 31.

The forward, cantilevered, or extended second end 60 of curved guide means 26 is provided with means 64 for securing cutting means 28 thereto. Securing means 64 may comprise an anchoring sleeve, collar, bearing, bushing, or other structure to hold and retain the leading, cutting portion 61 of cutting means 28 in place.

In one embodiment of the invention, curved guide means 26 comprises a channel 65. Curved guide means 58 is designed with elongated side walls at second end 60 that can be folded or bent over to form a collar, ring, conduit, or bore through which cutting portion 61 may pass and then be secured. In essence, the elongated side walls form a bearing surface within which cutting portion 61 may be held and/or rotated.

CUTTING MEANS

Cutting means 28 may comprise any apparatus or method which is capable of cutting or drilling material 31 within the confines of a curved bore. Traditional and/or nontraditional machining processes may be used, including mechanical, electrochemical, and thermal processes.

More particularly, the following processes may be used for cutting means 28: a mechanical rotating drill bit or burr; abrasive flow machining (AFM); fluid or water jet machining; abrasive water jet machining; hydrodynamic machining; ultrasonic machining (impact grinding and rotary ultrasonic machining); electrochemical machining (ECM); electrolytic hole machining using an apparatus sold by General Electric Company under the trademark ELECTROSTREAM; electron beam machining (EBM); laser beam machining (LBM); electric discharge machining (EDM); plasma beam machining (PBM); and/or plasma arc cutting (PAC). The above list of processes is not to intended to be limiting. Other processes may also be used.

As shown in FIGS. 1-5, 6 and 11-20, a rotary cutting means 66 may be used. Rotary cutting means 66 may comprise: cutting portion 61; a flexible drive shaft 68; a rigid drive shaft 70; and a conventional drive motor assembly 72.

Cutting portion 61 is defined by a rotary drill bit, burr, or the like, which when rotated and urged against material 31 is capable of boring into material 31. For example, cutting portion 61 may comprise a carbide, steel, diamond, or other hard material which is attached or welded to a terminal or distal end 74 of flexible drive shaft 68.

Cutting portion 61 has cutting edges 73 (not shown) formed therein. Cutting edges 73 may be formed either before or after cutting portion 61 is attached to flexible drive shaft 68. Where flexible drive shaft 68 comprises stainless steel or other metal, a portion of distal end 74 may be melted to form a hardened nugget 76 which is integral with a remaining portion of flexible drive shaft 68. Nugget 76 may then be machined to form cutting portion 61 and cutting edges 73.

A has been explained, distal end 74 of flexible drive shaft 70 is rigidly secured to cutting portion 61. Distal end 74 is rotatably secured to housing 36 by being inserted into and held by securing means 64.

To enable passage of curved guide means 26 through the aforementioned curved path within material 31, the crosssectional diameter of cutting portion 61 must be equal to or greater than the cross-sectional diameter of curved guide means 26. In essence, securing means 64 urges cutting portion 61 against and through material 31. Proper alignment and path direction is provided by the curvilinear design and rotational movement of curved guide means 26.

Flexible drive shaft 68 is generally a flexible drill shaft or shank which is initially retained within enclosure 38 of housing 36. As rocker arm 24 is pivoted, cutting portion 61, distal end 74 of flexible drive shaft 68, securing means 64, and curved guide means 26 are extended outwardly from within enclosure 38 through an opening in housing 36.

Channel 65 is designed to guide, receive, and retain a forward portion 78 of flexible drive shaft 68 a such forward portion 78 is extended outwardly from within enclosure 38. As forward portion 78 is received within channel 65 flexible drive shaft 68 is urged along the same curvilinear path as that experienced by curved guide means 26. Once cutting portion 61 begins to drill into material 31, flexible drive shaft 68 is further retained and supported by the interior sides of the bore created within material 31.

As shown in FIG. 1, flexible drive shaft 68 may initially move along a first direction or approach path and then be directed by curved guide means 26 to pass along a second or curvilinear path having a predetermined degree of curvature.

Figure 20:
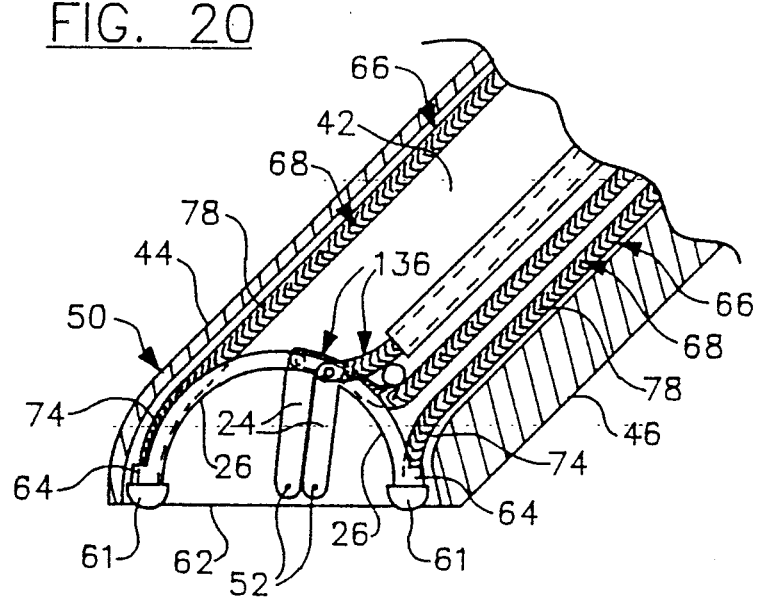
FIG. 20 is a partial, cross-sectional, side-elevational view of an eight embodiment of the present invention.

The first or approach path may be generally normal to a surface of material 31. Alternatively, the first approach path may be from any desired angle with respect to the surface of the material 31 to be drilled. FIG. 20 illustrates dual flexible drive shafts 68 whose initial orientation is not normal to the surface of material 31.

FIG. 1 illustrates a drilling apparatus 20 which will drill a curved bore that is generally located within a vertical plane. The curved bore begins within a third quadrant of a Cartesian coordinate system having its axis through pivot pin 52 and then passes upwardly into a second quadrant.

Figure 4:
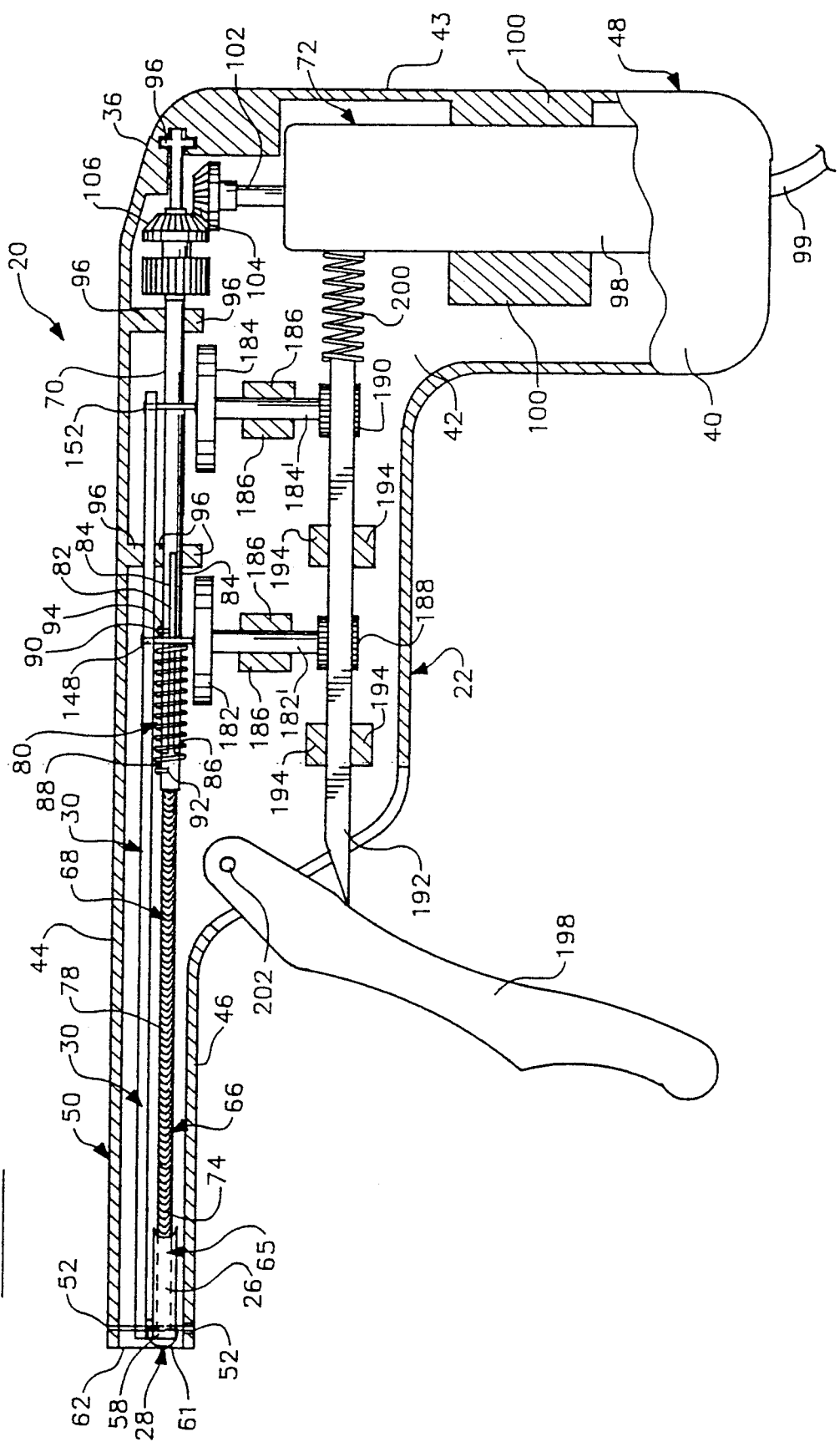
FIG. 4 is a partially sectioned, side-elevational view of a second embodiment of the invention, wherein the actuation means comprises a rack and pinion system.
Figure 5:
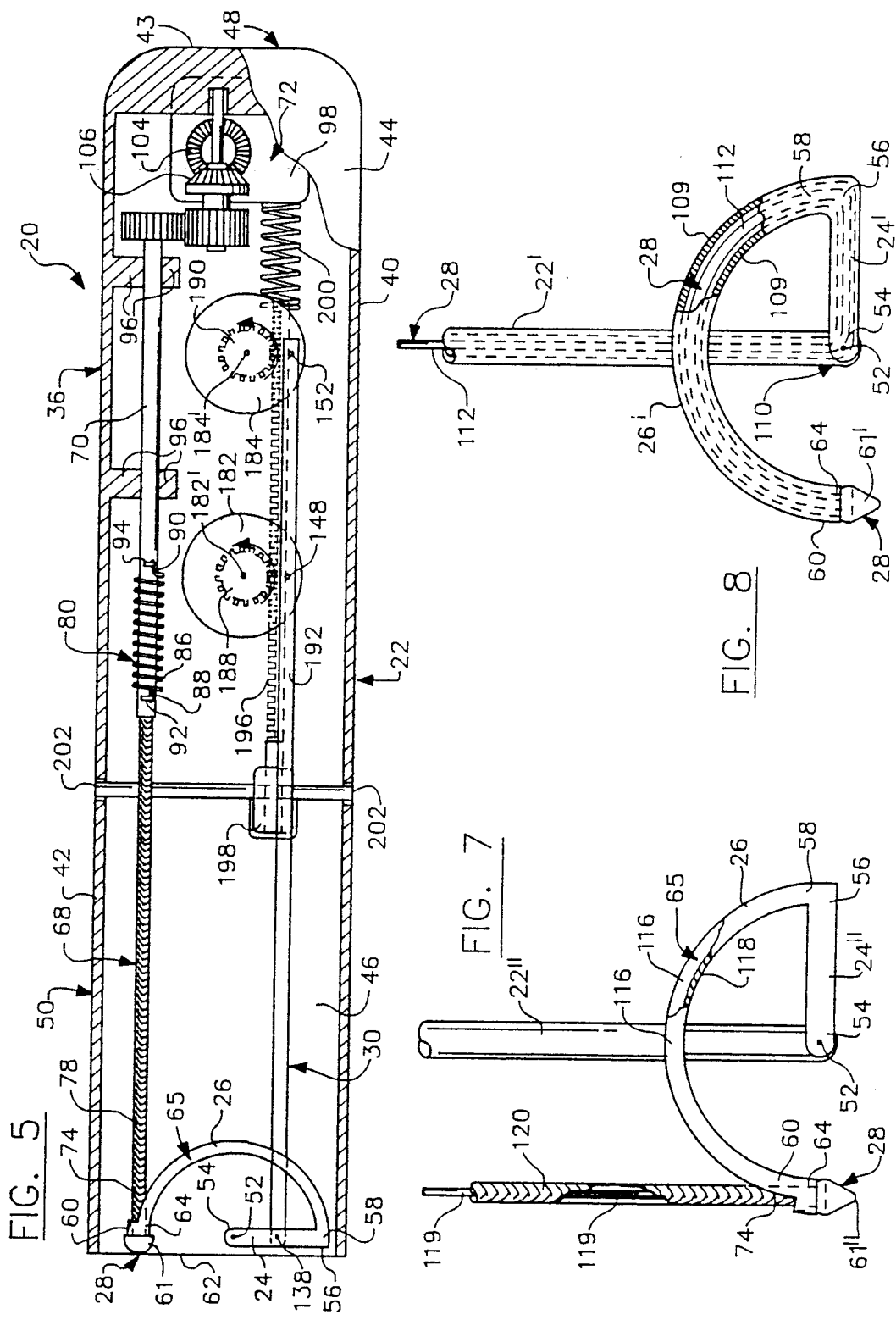
FIG. 5 is a partially sectioned, plan view of the second embodiment shown in FIG. 4 with a portion of the upper wall of the housing removed to better show the rack and pinion system.

FIGS. 4 and 5, illustrate another embodiment of drilling apparatus 20 which will drill a curved bore that is generally located within a horizontal plane. The curved bore begins within a second quadrant of a Cartesian coordinate system having its axis through pivot pin 52 and then passes sideways into a third quadrant.

Figure 6:
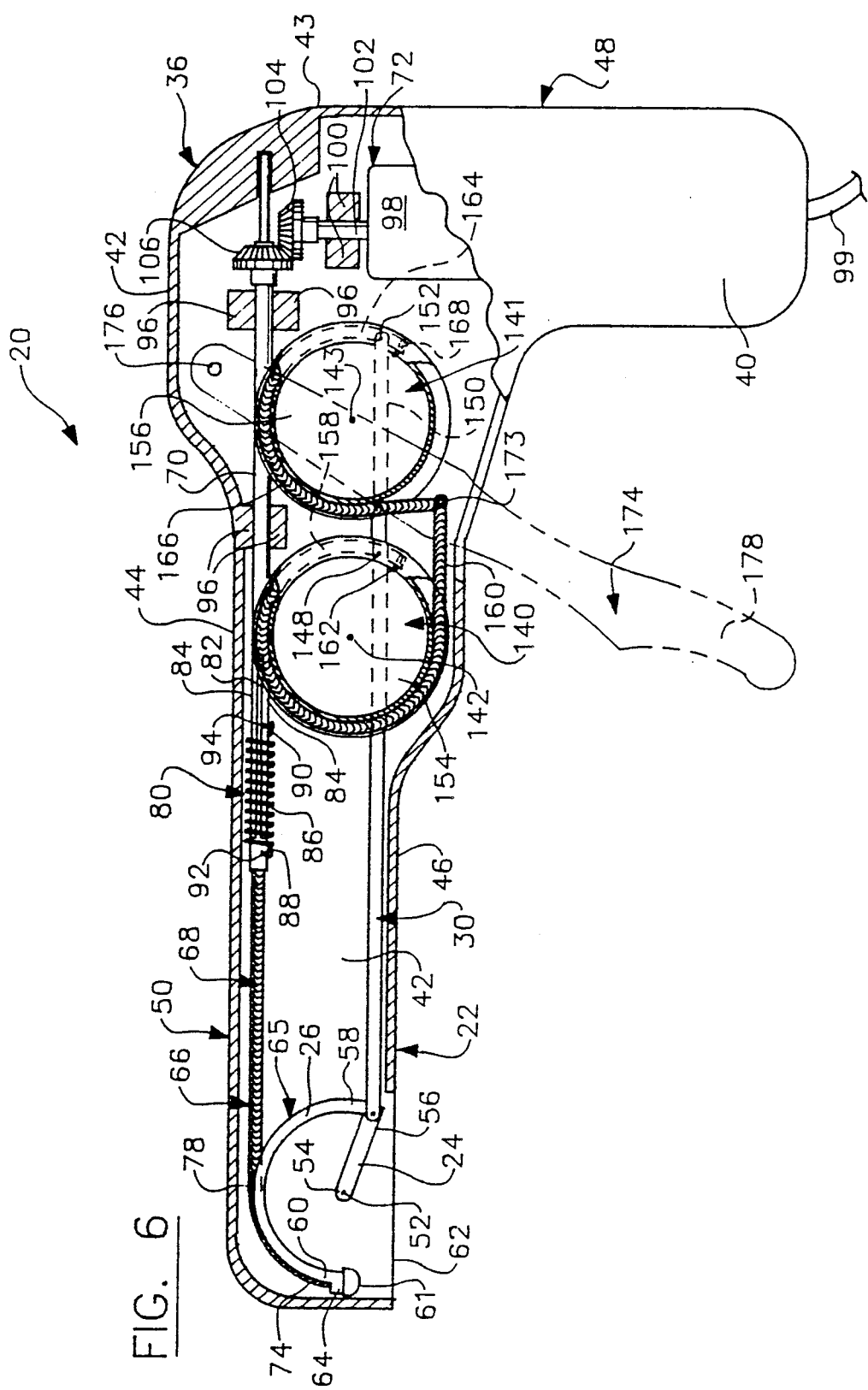
FIG. 6 is a side-elevational of third embodiment of the invention with a portion of the left wall of the housing removed.

FIG. 6 illustrates an embodiment, wherein a curved bore is generally located within a vertical plan, however, the curved bore begins within a third quadrant and passes into a forth quadrant.

Figure 11:
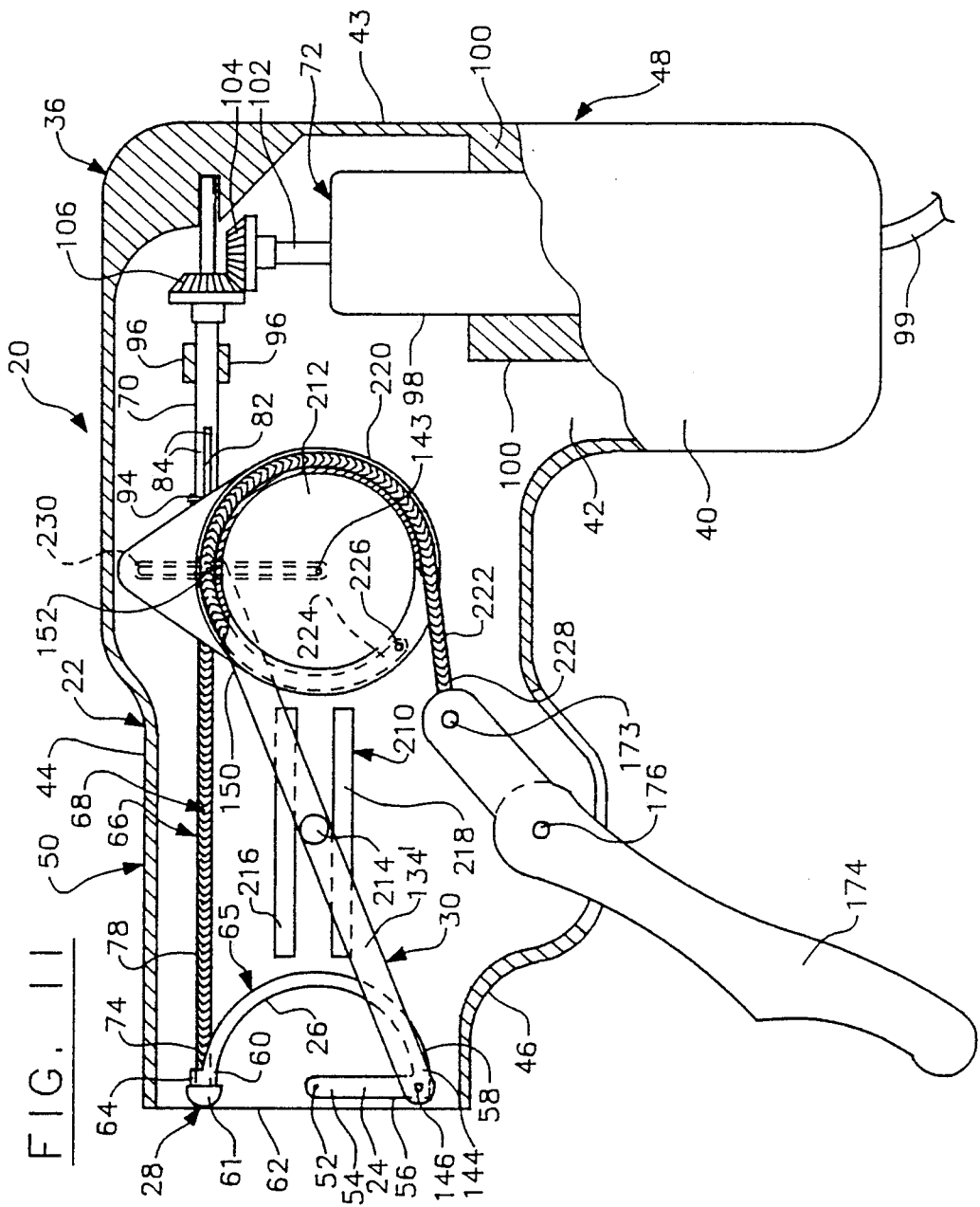
FIG. 11 is a partially sectioned, side-elevational view of a fifth embodiment of the present invention, wherein the actuation means comprises a crossed-crank mechanism.

FIG. 11 illustrates an embodiment, wherein a curved bore is formed within a vertical plane beginning within a second quadrant and passing into a third quadrant.

FIGS. 14-20 illustrate how rocker arm 24, curved guide means 26, securing means 64, and cutting portion 61 may pivot within one plane and the initial orientation or one or more flexible drive shafts 68 may be within a different plane.

Such embodiments are only illustrative. Many other orientations and cutting paths may be created using the claimed invention.

In summary, the present invention is not restricted to apparatus wherein flexible drive shaft 68 must pass from a rectilinear path to a curvilinear path. To the contrary, the initial orientation of flexible drive shaft 68 is only a matter of convenience. The primarily claimed invention is the system whereby a curved bore is formed.

Elongated flexible drive shaft 68 is operationally connected to an elongated rigid drive shaft 70 or shank which in turn is driven by a conventional drive motor assembly. The connection of flexible drive shaft 68 to rigid drive shaft 70 may comprise any method or apparatus which allows flexible drive shaft 68 to be extended into material 31. The process of drilling the bore necessarily requires flexible drive shaft to follow the urging and direction of curved guide means 26. If flexible drive shaft 68 is not provided with sufficient length, binding might occur.

In one embodiment, drilling apparatus 20 is provided with an expandable coupling 80 which connects flexible drive shaft 68 to rigid drive shaft 70. For example, expandable coupling 80 may comprise a pair of mated male 82 and female 84 elements. Male element 82 may have a square, rectangular, triangular, star-shaped, or other cross-sectional configuration which fits into a mated slot, bore, or canula within female element 84. The particular configuration is not necessarily important, just as long as the coupling or joint permits longitudinal expansion and still transmits rotational movement from rigid drive shaft 70 to flexible drive shaft 68.

Expandable coupling 80 may be spring-biased toward a closed, joined position. For example, a helical tension spring 86 may be provided to urge male element 82 into engaged contact with female element 84. Tension spring 86 also restricts lateral movement of flexible drive shaft 68 with respect to rigid drive shaft 70. As shown in FIG. 1, tension spring 86 may be placed around expandable coupling 80. Tension spring 86 may also be provided with offset hooks 88 and 90 which engage corresponding eyelets 92 and 94 on flexible drive shaft 68 and on rigid drive shaft 70, respectively.

One or more mounting brackets 96 used to support rigid drive shaft 70 for rotational movement may be attached to or incorporated within housing 36. Mounting brackets 96 are shown in FIGS. 1, 4-6 and 11-13. To present a clearer illustration of other elements, mounting brackets 96 have been omitted from the remaining Figures. Collars, bearings, bushings and/or other supporting structure (not shown) may also be used to assure proper orientation, and movement of rigid drive shaft 70. For example, means 96 to adequately restrict longitudinal and lateral movement of rigid drive shaft 70 should be provided.

Drive motor assembly 72 may comprise any one of many drive motor units. A wide variety of different drive motor units are commonly used within each particular industry. The type and size of drive motor assembly 72 will depend upon the availability of parts, preference of the user, and purpose for which drilling apparatus 20 is used. Within the surgical and dental professions, hand-held drive motor units are commonly used.

In one embodiment, a drive motor assembly having a controllable, powered, pneumatically driven motor 98 is used. For surgical environments, the inventor prefers to use a compressed, nitrogen pneumatic motor. Power is supplied to motor 98 through a power cord or hose 99 which may extend outwardly from within enclosure 38 of housing 36. Alternatively, electric or hydraulic drive motors may be used.

One or more mounting brackets 100 may be used to rigidly support motor 98 to housing 36. Motor 98 has a rotatable shaft 102 whereupon an angular coupling or gear connection is provided to transfer rotational movement from rotating shaft 102 to rigid drive shaft 70. As shown in FIG. 1, a pair of meshed bevel gears 104 and 106, having intersecting axes are rigidly attached to rotatable shaft 102 and to rigid drive shaft 70, respectively. Rotation of shaft 102 turns bevel rear 104, which in turn engages and rotates bevel gear 106 and rigid drive shaft 70. Other gear systems and angular couplings could also be used.

In another embodiment, cutting means 28 may utilize an electric discharge machining (EDM) process to create a curved bore. A drilling apparatus 20 which uses this process is illustrated in FIGS. 9 and 10.

Electric- or electro- discharge machining (EDM) cuts metal by discharging electric current stored in a capacitor bank (not shown) across a thin gap between a tool or cutting portion 61 (cathode) and material 31 (anode). Literally thousands of sparks per second are generated and each spark produces a tiny crater by melting and vaporizing the metal, thus eroding the shape of cutting portion 61 into material 31.

Cutting portion 61 may be made of a variety of materials, including: graphite, copper, brass, coppertungsten, aluminum, 70/30 zinc tin, and other alloys. Graphite, is the preferred material. The choice of material for a particular application depends upon such factors as: how easily can cutting portion 61 be machined from the material; how fast such material wears, or how susceptible the material is to spark erosion; how fast the particular material cuts; what kind of quality of finish can be produced; what type of power supply is needed and/or is available; and how much the material costs.

The distance between cutting portion 61 and the nearest surface of material 31 represents the overcut and is equal to the length of the spark. The length of the spark is essentially constant over all areas of cutting portion 61, regardless of its size or shape. Typical overcut values range from 0.0005 to 0.020 inches. Overcut depends on the gap voltage and amperage. With proper tooling, the crosssectional dimension of cutting portion 61 is basically equal to the desired dimension of the part less the overcut value.

Material 31 may be immersed within a dielectric fluid 108 which in turn is retained within a container 109 (shown in FIGS. 9 and 10). Dielectric fluid 108 is used to: provide insulation properties between curved guide means 26 and material 31; confine the sparks within a local area immediately adjacent to cutting portion 61; serve as a conductor for the sparks between cutting portion 61 and material 31; serve as a coolant or heat bank to cool down rocker arm 24, curved guide means 26, securing means, and portions of cutting means 28; and to flush out debris located between cutting portion 61 and material 31.

Dielectric fluid 108 must ionize to provide a channel for the spark and then quickly deionized to become an insulator at further distances from cutting portion 61. Polar compounds, like glycerine-water (90:10) with triethylene oil as an additive, may be used. Alternatively, traditional cutting fluids like kerosene may be used.

Electric discharge machining (EDM) allows each spark to contain a discrete, measured, and controlled amount of energy. This enables the cutting speed and surface finish to be accurately predicted, and the size of the bore can be carefully controlled. The heat generated by the sparks melts the metal, and the impact of the spark causes the metal to be ejected, vaporized, and recast within dielectric fluid 108 as spheres. Material 31 of any hardness can be cut using this process, as long as the material can conduct electricity.

Electric discharge machining (EDM) removes almost all mechanical forces which would otherwise be required to drill a bore. Thus, fragile parts may be easily tooled with the present invention using and EDM process.

Increased controllability, versatility, and accuracy of the EDM process allows the present invention to drill curved bores in carbides, steels, and metals of any hardness, significantly reducing the cost that would otherwise be required to manufacture tools and dies to achieve a similar result.

As shown in FIG. 8, some processes allow a portion of cutting means 28 to be placed and contained within a hollow, interior cavity of an arcuate, tubular, curved guide means 26'. Rocker arm 24' and support structure 22' may also comprise tubular members. Outer walls 109 of curved guide means 26' serve to protect and insulate cutting means 28.

An appropriately designed pivotal connection 110 may be provided at or near pivot pin 52 to transfer cutting power from a remote power source (not shown) to a leading, boring tip or cutting portion 61' which is secured near second end 60 of curved guide means 26'. Pivotal connection 110 may be any one of a multitude of connections which are commonly known and used within mechanical engineering.

For example, if electric discharge machining (EDM) processes are used, pivotal connection 110, which transfers electrical power from a remote power source (not shown) to cutting portion 61' without interruption of electrical current during pivotal movement of rocker arm 24', may be used. A wire 112 may be placed within a hollow, interior conduit of a tubular support structure 22', rocker arm 24', and curved guide means 26'. This greatly reduces and insulates the exposed portions of drilling apparatus 20.

Similarly, a pivotal connector with transfers optical transmissions, such as laser power, may also be used.

As shown in FIG. 7, curved guide means 26 may alternatively have an outwardly extending, arcuate, receiving channel 65 defined by sidewalls 116 and base 118. Receiving channel 65 is used to guide, receive, and retain a flexible portion of cutting means 28. Thus, cutting portion 61 may be directly connected to a remote power source (not shown).

For example, a flexible optical conduit 119 may be enclosed within a protective insulator 120. Optical conduit is then connected to a source of laser light (not shown). As rocker arm 24 pivots about pivot pin 52, which is held in position by support structure 22'', curved guide means 26 and cutting portion 61'' are advanced toward material 31. The motion and path of curved guide means 26 cause optical conduit 119 and protective insulator 120 to be guided, received, and retained within channel 65.

Channel 65 may also be used with a rotary cutting portion 61, and flexible drive shaft 68 as shown in FIGS. 1-6.

Whether the curved guide means is a tube or channel largely depends upon the cutting and machining process used.

Thus, when rocker arm 24 is pivoted, curved guide means guides and advances cutting means 28 away from support structure 22 to bore a hole along a predetermined curved path within material 31.

After the bore has been created, the motion of rocker arm 24 is reversed and curved guide means 26 and cutting means 28 are removed from within material 31. The insertion and retraction of curved guide means 26 and cutting means 28 into and from material 31 is defined by the oscillation of rocker arm 24.

When rocker arm 24, curved guide means 26, and cutting portion 61 of cutting means 28 lie within a common plane, curved bores may be created which have up to a 180 degree rotation. In other words, the length of the curved bore may generally be determined by multiplying the length of rocker arm 24 between pivot pin 52 and the center of the rigidly attached curved guide means 26 by a value of $\pi$.

Alternatively, rocker arm 24, curved guide means 26, and cutting portion 61 may define a helical drilling apparatus 20 which forms a cylindrical spiral bore. This may be accomplished by securing a helically shaped curved guide means (not shown) to the extended second end 56 of rocker arm 24. Cutting portion 61 is secured to the cantilevered second end 60 of curved guide means 26. This design enables rocker arm 24 to be pivoted more than 360 degrees and to actually serve as a crank, screwing cutting portion 61 and curved guide means 26 into the material. Of course, rocker arm 24 would necessarily have to move along its axis of rotation towards material 31 as curved guide means 26 is inserted into material 31.

ACTUATION MEANS

Pivotal rocker arm 24, curved guide means 26, and cutting means 28 may be remotely actuated by an actuation means which simply is a drill guide advancing mechanism. Such actuation means selectively urges rocker arm 24 to pivot or rotate, thereby urging curved guide means 26 and cutting means 28 to advance toward material 31 and bore a hole along a predetermined curved path within material 31. Such actuation means may also be used to retract rocker arm 24 to an initial position and thereby withdraw curved guiding means 26 and cutting means 28 from within material 31. The insertion and retraction of curved guide means 26 and cutting means 28 into and from material 31 defines an oscillation of rocker arm 24.

Pivotal rocker arm 24, curved guide means 26, and cutting means 28 may be remotely actuated by a wide variety of actuation means 30.

As illustrated in FIGS. 9 and 10, actuation means 30 may simply comprise tension or compression spring 122 having a first end or arm 124 and a second end or arm 126. First end or arm 124 is urged against rocker arm 24. Second end or arm 126 is urged against support structure 22. Thus, the tensile or compression forces stored within spring 122 urge spring 122 either open or closed, depending upon whether spring 122 is a compression or tension spring. In either case, the forces stored within spring 122 should urge rocker arm 24, curved guide means 28, and cutting means 28 to rotate about pivot pin 52.

In one embodiment, spring 122 is a tension spring which urges cutting means 28 toward and/or against material 31. During operation, rocker arm 24 is pivoted clockwise as shown by arrow 128. This raises cutting portion 61 above an upper surface of material 31. Manual forces exerted on rocker arm 24 are then released so that spring 122 may pivot rocker arm 24 in a counterclockwise direction, thereby urging cutting portion 61 into close proximity with the upper surface of material 31.

Additional elements may be used to enable cutting portion 61 to be retracted from within material 31 without necessitating that an operator reach into dielectric fluid 108 to rotate rocker arm 24 in a clockwise direction. For example, first end 54 of rocker arm 24 may be rigidly attached to a first end of an elongated pivot pin 52. Pivot pin 52 may be protected and insulated within an outer sheathing 129. Pivot pin 52 is then rotatably secured to support structure 22. A lever or crank 130 is rigidly attached to a second end of pivot pin 52. Rigid attachment may be accomplished by any appropriate means. In FIG. 10, nut 131 and washers 132 are threaded onto the first and second ends of pivot pin 51. Other means of attachment, such as by welding, may also be used.

Rotation of crank 130 causes pivot pin 52 to rotate within support structure 22, and thereby urge rocker arm 24 to rotate in a similar direction. Rotation of rocker arm 24 causes curved guide means 26 and cutting means 28 to advance or retract, depending upon the direction of rotation, through the predetermined curved path.

Other forms of actuation means 30 may also be used. For example, FIGS. 1-6, 11-13, 14-16, 17-19, and 20 illustrate different types of connecting rods 134 and push/pull flexible linkages 136 that may be pivotally secured to either rocker arm 24 or to curved guide means 26. Preferably, connecting rods 134 or flexible linkages 136 are secured to rocker arm 24 at a juncture or intersection of rocker arm 24 with curved guide means 26. Alternatively, as shown in FIG. 5, connecting rod 134 may be connected to rocker arm 24 at an intermediate point 138 between first end 54 and second end 56.

Appropriate movement of connecting rod 134 or flexible linkage 136 causes rocker arm 24, curve guide means 26, and cutting means 28 to advance or retract through a predetermined curved path.

FIGS. 1-3 illustrate a first embodiment of the present invention, wherein actuation means 30 comprises a double parallel-crank mechanism. Rocker arm 24, and two different crank systems 140 and 141 are rotationally secured to support structure 22, in such a manner that their axes are located along a common ray or line. First crank system 140 rotates about a pivot pin 142. Second crank system 141 rotates about a pivot pin 143.

A single connecting rod 134 is connected to rocker arm 24 and to each of the two crank systems 140 and 141. A first end 144 of connecting rod 134 is pivotally secured to second end 56 of rocker arm 24. A pivot pin 146 is used to secure connecting rod 134 to rocker arm 24.

Connecting rod 134 is pivotally secured to a first crank system 140 at an intermediate location along the length of connecting rod 134. Pivot pin or rivet 148 may be used to secure connecting rod 134 to first crank system 140. The distance between pivot pin 142 and pivot pin 148 is substantially equal to the distance between pivot pin 52 and pivot pin 146.

A second end 150 of connecting rod 134 is pivotally connected to second crank system 141 by means of a pivot pin 152. Similarly, the distance between pivot pin 143 and pivot pin 152 is substantially equal to the distance between pivot pins 52 and 146, and between pivot pins 142 and 148.

The distance between pivot pins 146 and 148 is substantially equal to the distance between pivot pins 52 and 142. Likewise, the distance between pivot pins 148 and 152 are substantially equal to the distance between pivot pins 142 and 143.

In essence, support structure 22, rocker arm 24, connecting rod 134, first crank system 140, and second crank system 141 move within parallel planes and form a plane parallelogram.

Connecting rod 134, first crank system 140, and second crank system 141 may be of any form or configuration so long as such elements perform the described function and do not interfere with the desired motion.

Connecting rod 134 is capable of rotating freely about pivot pins 146, 148, and 152, even through a complete rotation of 360 degrees if need be. In most cases, however, rotation will be limited to 180 degrees.

Movement of either first crank system 140 or of second crank system 141 will cause connecting rod 134 to transmit substantially identical rotational movement to rocker arm 24.

Means for rotating first and/or second crank systems 140 and 141 are also provided.

First and/or second crank systems 140 and 141 may have one or more pulleys incorporated therein. Such pulleys share the similar axis of rotation as their corresponding crank system. As shown in FIGS. 1-3, first and second crank systems 140 and 141 comprise pulleys 154 and 156, respectively.

Pulleys 154 and 156 have outwardly extending channels of substantially similar diameter within which one or more flexible tension cords, chains, cables, or the like may be placed. The pulleys and flexible tension cords provide smooth, easy actuation and rotation of the plane parallelogram, attached curved guide means 26, and cutting means 28.

As shown in FIG. 1, a first end 158 of a first tension cord 160 is secured pulley 154 by fastener 162. Similarly, a first end 164 of a second tension cord 166 is secured to pulley 156 by fastener 168. Flexible tension cords 160 and 166 run within the exterior channels of pulleys 154 and 156, respectively. A second end 170 of first tension cord 160 and/or a second end 172 of second tension cord 164 are rigidly secured by a fastener 173 to an easily controlled trigger 174, lever, switch, or the like.

Trigger 174 extends outwardly from within enclosure 38 and is pivotally secured by pivot pin 176 to support structure 22. Pivot pin 176 is positioned in such a manner as to give mechanical advantage to an extended portion 178 of trigger 174.

Pivotal movement of extended portion 178 about pivot pin 176 causes fastener 173 to move through an predefined arc or path which is defined by the angle of rotation and radial distance between pivot pin 176 and fastener 173. Movement of fastener 173 causes tension cords 160 and 166 to move longitudinally, which in turn rotate pulleys 154 and 156. Pulleys 154 and 156 are rotated at substantially the same rate, thereby causing connecting rod 134 to rotate rocker arm 24, curved guide means 26, and cutting means 28.

A tension spring 180 may be operationally secured to support structure 22 to urge first and/or second crank systems 140, 141 toward rotation or to retract crank systems 140 and 141 from an earlier rotation. One end of tension spring 180 may be secured to pivot pin 143, which in turn is rigidly fixed to support structure 22. The other end of tension spring 180 may be secured to pulley 156.

It is important to note, that at its critical position, where connecting rod 134 and pivot pins 52, 142 and 143 all lie within a substantially similar ray or line, flexible tension cord 160 continues to exert a force upon first crank system 140, and tension cord 166 exerts a force upon second crank system 141. Because of this design, actuation means 30 has no uncertainty of motion at such a position. In other words, there are no dead points.

FIG. 6 illustrates an alternative position for trigger 174, pivot pin 176, and fastener 173. As can be seen, the rotational direction of first and second crank systems 140 and 141 depend upon the desired motion for actuation and path of rocker arm 24.

In a second embodiment of the present invention, as illustrated in FIGS. 4–5, the pulleys 154 and 156, and tension cords 160 and 166 of the first embodiment are replaced with a rack and pinion system. In this second embodiment, first crank system 140 and second crank system 141 comprise disks 182 and 184 which are connected to connecting rod 134 by pivot pins 148 and 152, respectively. Disk 182 is rigidly secured to a shaft 182'. Shaft 182' is rotationally secured to support structure 22 by brackets 186. Disk 184 is rigidly secured to a shaft 184'. Shaft 184' is also rotationally secured to support structure 22 by brackets 186. A first pinion 188 is rigidly secured to shaft 182' of first crank system 140. A second pinion 190 is rigidly secured to shaft 184' of second crank system 141.

A rack 192 is located within enclosure 38 and is secured to support structure 22 in such a way as to enable rack 192 to slide back and forth within fixed guides 194. Rack 192 has rack teeth 196 which mesh with pinions 188 and 190. When rack 192 slides within fixed guides 194, rack teeth 196 cause pinions 188 and 190, shafts 182' and 184', and disks 182 and 184 to rotate, which in turn drive connecting rod 134. Movement of connecting rod 134 causes rocker arm 24, curved guide means 26, and cutting means 28 to pivot within their predetermined curved path.

Rack 192 is held in operable contact with a lever 198 by a compression spring 200. Lever 198 pivots about a pivot pin 202.

Figure 12:
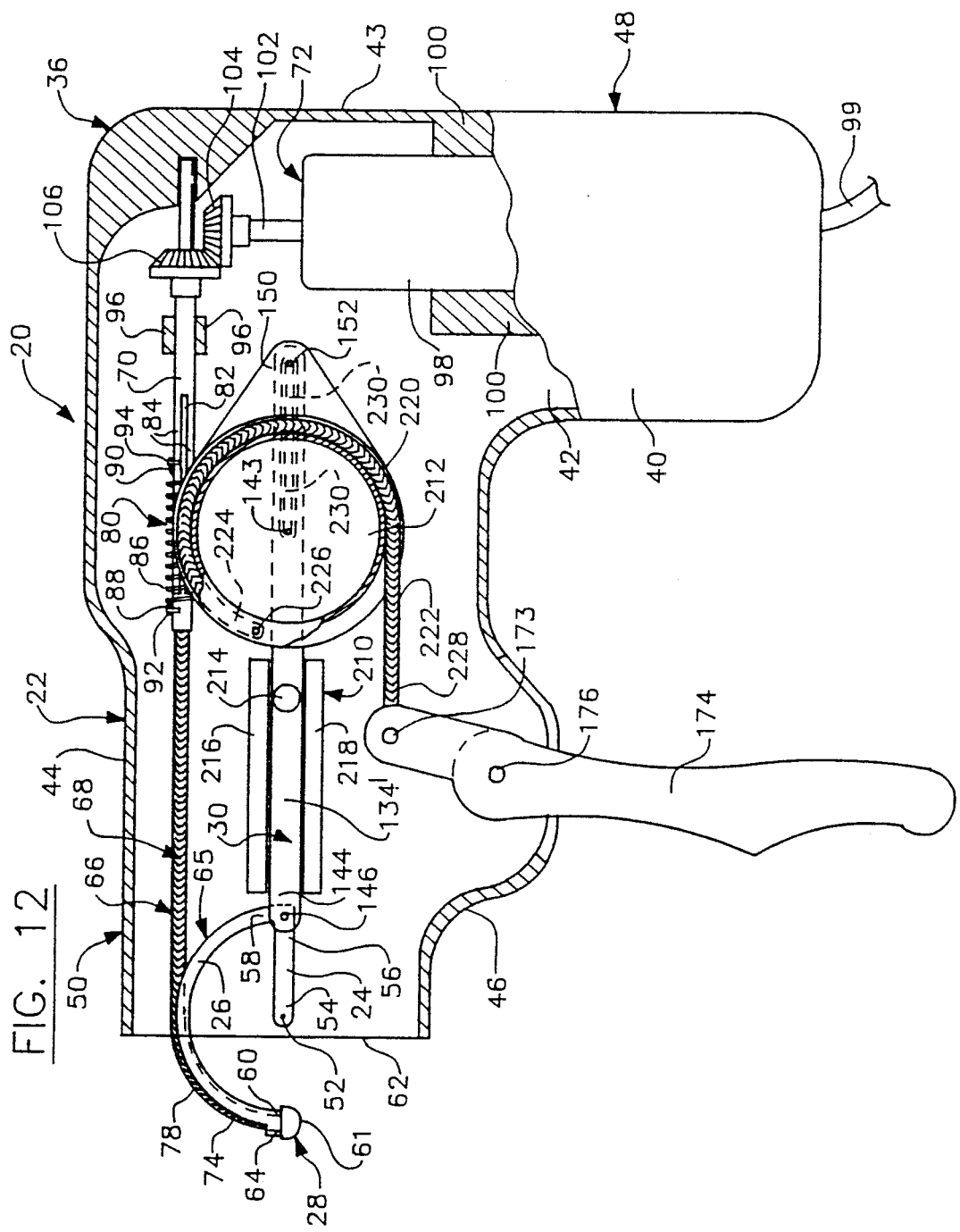
FIG. 12 is a partially sectioned, side-elevational view of a fifth embodiment shown in FIG. 11, wherein the rocker arm and curved guide means are partially rotated to extend the cutting means past the support structure along a predetermined curved path.
Figure 13:
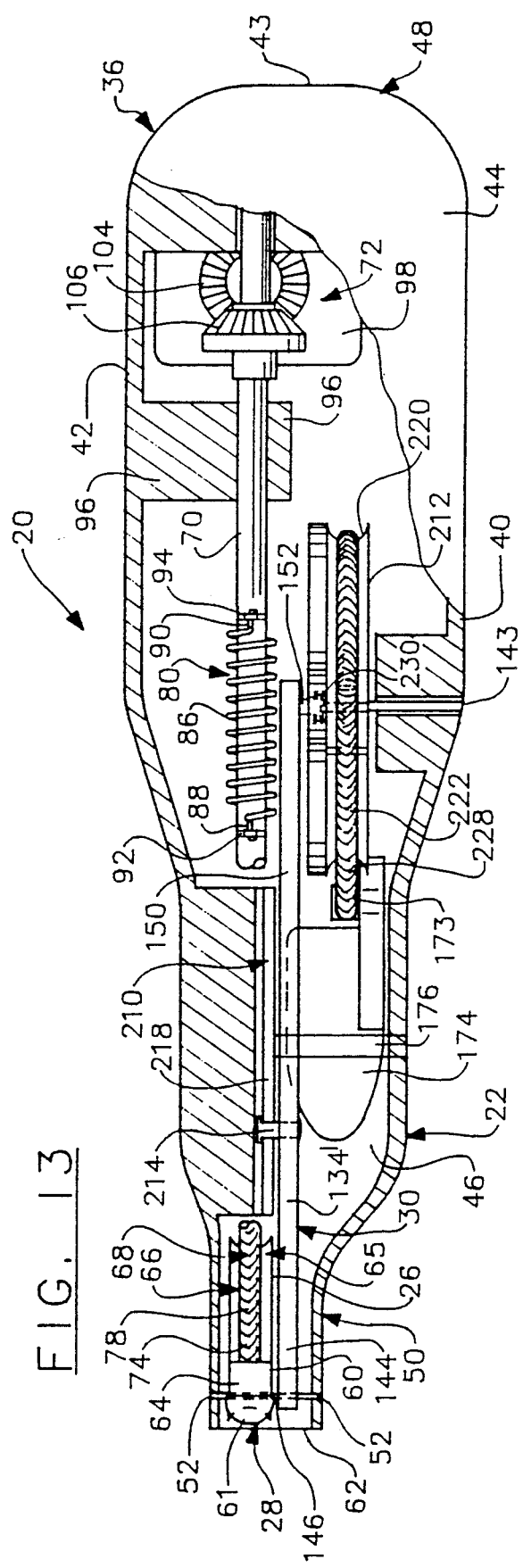
FIG. 13 is a partially sectioned, plan view of the fifth embodiment as shown in FIG. 11.
Figure 14:
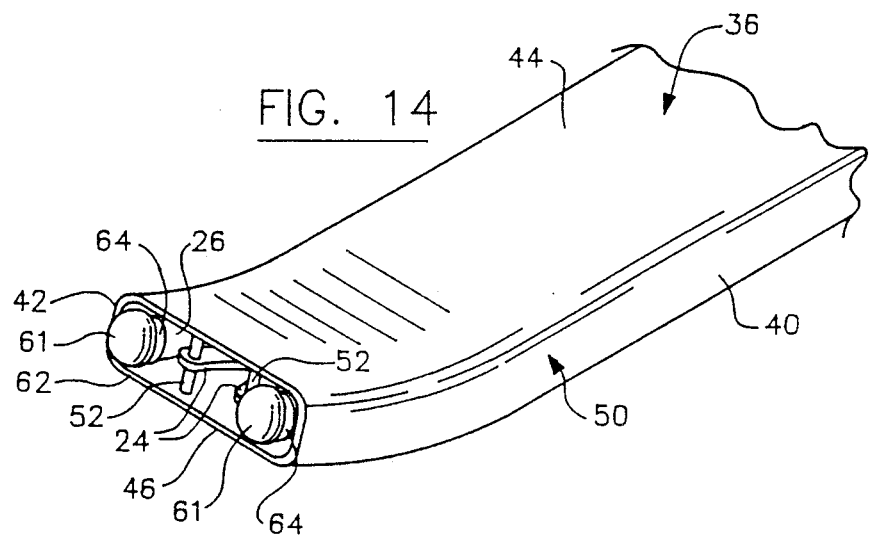
FIG. 14 is a partial, isometric view of a sixth embodiment of the invention as seen in FIGS. 15 and 16.
Figure 15:
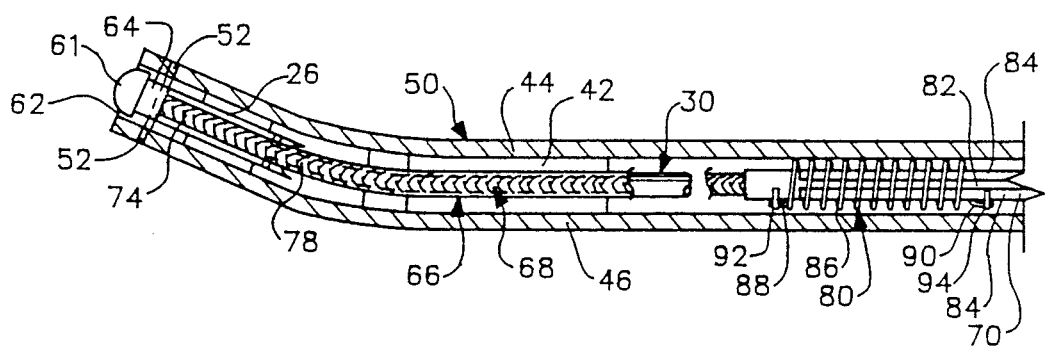
FIG. 15 is a partial, cross-sectional, side-elevational view of the sixth embodiment shown in FIGS. 14 and 16, wherein the rocker arm, curved guide means, and cutting head pivot within a plane that is different from that of the rigid drive shaft.

In a further embodiment, illustrated in FIGS. 11–13, actuation means 30 may comprise a crossed-crank mechanism, having: a rotatable disk crank 212; a levered connecting rod 134'; a guide 210; and trigger 174.

Disk crank 212 is rotatably secured to support structure 22 and pivots about pivot pin 143.

A first end 144 of levered connecting rod 134' is secured to rocker arm 24 by pivot pin 146. A second end 150 of levered connecting rod 134' is secured to rotating disk crank 212 by pivot pin 152.

Levered connecting rod 134' is also provided with a slidable slide or pivot pin 214 at some intermediate point between first end 144 and second end 150. Preferably, slidable pivot pin 214 is located at a midpoint between first end 144 and second end 150.

Slidable pivot pin 214 is placed within a guide 210 having an upper portion 216 and a lower portion 218. As slidable pivot pin 214 slides within guide 210, upper portion 216 and lower portion 218 serve as fulcrums against which levered connecting rod 134' is urged. The fulcrums are defined by interior side walls of a groove, slot, or channel of guide 210 formed within or secured to support structure 22. The fulcrums provide a rigid point of support about which connecting rod 134' may pivot.

Similar to the explanation given above, disk crank 212 may be provided with a pulley 220 which rotates about pivot pin 143. Pulley 220 has an outwardly extending channel within which a flexible tension cord 222 may be received, guided, and stored.

Flexible tension cord 222 has a first end 224 which is attached to pulley 220 by a fastener 226. A second end 228 of flexible tension cord 222 is attached to trigger 174 by fastener 173. Trigger 174 pivots about a pivot pin 176 to impart a tension and movement within cord 222. As a result of the movement of trigger 174, disk crank 212 is rotated.

The distance between pivot pins 52 and 146 is substantially similar to the distance between pivot pins 143 and 152.

In one embodiment (not shown), the distance between pivot pins 146 and 152 is substantially equal to the distance between pivot pins 52 and 143. Were this so, a true crossed-crank mechanism would be created.

In an alternative embodiment, shown in FIGS. 11–13, a modified crossed-crank mechanism is illustrated. Generally, a slot 230 is provided within disk crank 212, and pivot pin 152 is free to slide within slot 230. Disk crank 212 is also elongated adjacent to slot 230 to provide support and clearance for slot 230. This design permits a lesser tolerance to be used between the various parts of the apparatus.

As trigger 174 is pivoted about pivot pin 176, fastener 173 pulls on tension cord 222 which in turn rotates disk crank 212. As disk crank 212 rotates, pivot pin 152 is allowed to freely slide within slot 230. Tangential forces upon pivot pin 152 force connecting rod 134' to rotate about pivot pin 214. Pivot pin 214 is also able to freely slide within guide 210. Guide 210 serves as a fulcrum against which connecting rod 134' is urged. Further rotational movement of disk crank 212 is transmitted through connecting rod 134' to cause rocker arm 24 to move with generally the same motion as disk crank 212, except in an opposite rotational direction.

FIG. 12 illustrates this embodiment with a partially extended condition. Further rotation of disk crank 212 forces connecting rod 134' to push against pivot pin 146 and force rocker arm further upward within its predetermined curved path.

Similar to the above description, a spring (not shown) may be used to urge disk crank 212 toward rotation or toward a retractation from an earlier rotation. The spring should be operationally secured between support structure 22 and disk crank 212.

In still further embodiments, as shown in FIGS. 10, 14–20, multiple rocker arms 24, multiple curved guide means 26, multiple cutting means 28, and multiple actuation means 30 may be used in unison or within a single apparatus.

FIG. 10 illustrates many drilling apparatus 20 being used in unison.

FIGS. 14–20 illustrate multiple drilling apparatus used within a single apparatus.

Figure 16:
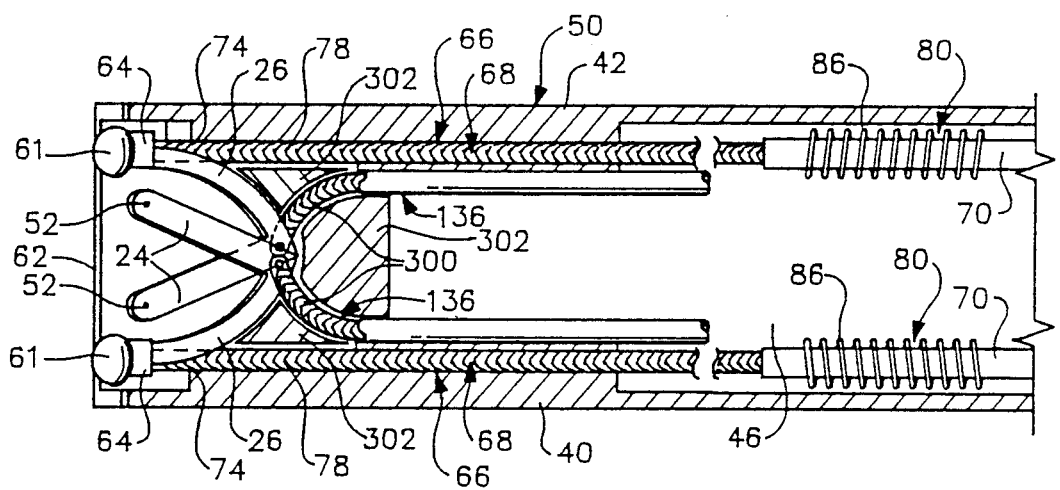
FIG. 16 is a partial, cross-sectional, plan view of the sixth embodiment shown in FIGS. 14 and 15 with an upper wall of the housing removed to illustrate use of multiple rocker arms, curved guide means, cutting means, and actuation means within a single apparatus.

More particularly, FIG. 16 illustrates how two off-centered pivot points 52 may be used to form a wishbone shaped bore.

Of particular interest is how a flexible push/pull linkage 300 may be used actuate the rotational movement of rocker arm 24. Appropriate guides 302 are provided to properly direct the forces transmitted within flexible linkage 300.

The present invention also allows cutting means 28 to have a wide range of orientations with respect to the bored surface of material 31. This is accomplished by controlling the path and angle of rotation of curved guide 26 and cutting means 28, and by placing curved guide means 26 and cutting means 28 at various angles with respect to the remaining elements of drilling apparatus 20 and/or with respect to material 31 to be drilled.

FIG. 19 illustrates a mechanism which has an actuating means 30 similar to that described in the parent U.S. patent application. The differences, however, accentuate the fact that a linear to a curvilinear path for the flexible drill shaft is not necessary or required. These drawings depict only a few of several different types of apparatus that may be created wherein the flexible drill shaft pass from a curvilinear path to a curvilinear path.

Thus, with the present invention, an incision may be made at a considered safe location and then the drilling means may be appropriately positioned near or against the bone structure to be drilled. Once in position, the drilling may take place without having to move or manipulate the position of drilling apparatus 20.

The means and construction disclosed herein are by way of example and comprise primarily the preferred form of putting the invention into effect. Although the drawings depict a preferred and alternative embodiments of the invention, other embodiments have been described within the preceding text. One skilled in the art will appreciate that the disclosed device may have a wide variety of shapes and configurations. Additionally, persons skilled in the art to which the invention pertains might consider the foregoing teachings in making various modifications, other embodiments, and alternative forms of the invention.

It is, therefore, to be understood that the invention is not limited to the particular embodiments or specific features shown herein. To the contrary, the inventor claims the invention in all of its forms, including all alternatives, modifications, equivalents, and alternative embodiments which fall within the legitimate and valid scope of the appended claims, appropriately interpreted under the Doctrine of Equivalents.

INDUSTRIAL APPLICABILITY

The present invention may be used within a wide variety of industries, wherein simple, reliable, easily used apparatus and methods are needed to form one or more curved bores within a solid material. The apparatus of this invention is also compact, functional, unobtrusive, efficient, reusable, durable, rugged, is easily constructed, and is inexpensive and economical to manufacture. Traditional or nontraditional drilling processes may be used. The present invention not only increases the speed and simplifies the procedure to form curved bores, it also provides an drilling apparatus which requires less access room for operation and does not damage adjacent material. This invention also allows drilling to be initiated from a wide range of orientations with respect to the bored surface.

Although the invention has a wide range of applications, the invention has special application in surgical procedures, wherein a ligament, tissue, wire, or other element must be secured to a bone surface. The present invention permits such procedures to be accomplished in areas of extremely limited access. The curved bore may be produced even within a very small, deep access opening or incision, with minimum damage to adjacent bone structure and soft tissue. Once the curved bore is formed, a suture or other attaching filament may be easily passed through the bore to anchor the tissue or ligament to the bone.

What is claimed is:

1. An apparatus for drilling a curved bore within a material comprising:

(a) a support structure having a fixed orientation with respect to said material;

(b) a rocker arm pivotally secured to said support structure at a fixed pivot point, said fixed pivot point defining an axis of rotation, said rocker arm defining a rotating link or crank which rotates or oscillates about said fixed pivot point, said rocker arm having a first end located near said fixed pivot point and having a second end extending radially outward from said fixed pivot point;

(c) curved guide means defining an arcuate tube or channel having a first end rigidly attached to or integral with said second end of said rocker arm, said curved guide means having an extended second end which cantilevers outwardly from said rocker arm, said curved guide means generally laying within an arc defined by a rotational path of said second end of said rocker arm as said rocker arm is rotated about said fixed pivot point, said pivot point being located near a protrusion or edge of said support structure in such a manner that when said rocker arm is pivoted or rotated, said second end of said curved guide means extends away from said support structure passing through a predetermined curved path;

(d) means for cutting said material within confines of said curved bore;

(e) means for securing said cutting means to said second end of said curved guide means, said securing means comprising a bearing, a bushing, or other structure to hold and retain said cutting means in place, said curved guide means having an arcuate tube or channel incorporated therein; and (f) means for remotely actuating rotation of said rocker arm, said actuation means selectively urging said rocker arm to pivot or rotate thereby urging said curved guide means and said cutting means to advance toward said material to bore a hole along said predetermined curved path within said material or to retract said rocker arm to an initial position thereby withdrawing said guiding means and said cutting means from within said material, insertion and retraction of said curved guide means and said cutting means into and from said material being defined by an oscillation of said rocker arm.

2. The apparatus of claim 1, wherein said support structure comprises: an independent, dedicated support stand; an extension from a separate structure; or a hand-held housing unit.

3. The apparatus of claim 1, wherein said fixed pivot point comprises a pivot pin which pivotally secures said rocker arm to said support structure.

4. The apparatus of claim 1, wherein said cutting means incorporates therein a mechanical, electrochemical, or thermal machining process.

5. The apparatus of claim 4, wherein said cutting means comprises a rotary cutting means.

6. The apparatus of claim 4, wherein said process comprises an electric discharge machining (EDM) process.

7. The apparatus of claim 1, wherein a portion of said cutting means is placed and contained within a tubular cavity of said curved guide means.

8. The apparatus of claim 7, further comprising a powered pivotal connection located at said fixed pivot point of said rocker arm between said support structure and said cutting means, said powered pivotal connection transferring power from a remote power source to a leading, boring tip or cutting head secured near said second end of said curved guide means.

9. The apparatus of claim 1, wherein said cutting means comprises a flexible shaft which is directly connected to a remote power source, said curved guide means having an outwardly extending receiving channel into which said flexible shaft of said cutting means is guided, received, and retained, said channel receiving and retaining said flexible shaft as said cutting means and said curved guide means advance toward and through said material.

10. The apparatus of claim 9, wherein said cutting means comprises a remote rotational power source, a flexible drill shaft, and a leading cutting head, said rotational power source transmitting rotation force through said flexible drill shaft to rotate said leading cutting head, said securing means of said curved guide means permitting rotation of said leading cutting head, said curved guide means having an exterior channel into which said flexible drill shaft is guided, received and retained.

11. The apparatus of claim 1, wherein said rocker arm, said curved guide means, and said cutting head of said cutting means lie within a common plane.

12. The apparatus of claim 1, wherein said rocker arm, said curved guide means, and said cutting head define a helical boring apparatus which forms a cylindrical spiral bore, said curved guide means having a helically-shaped curved guide means attached to said extended second end of said rocker arm, said cutting head being secured to said cantilevered second end of said curved guide means, said rocker being capable of pivoting more than 360 degrees in rotation to serve as a crank to screw said cutting head and said curved guide means into said material, said rocker arm being moved along said axis of rotation towards said material as said cutting head and said curved guide means are inserted into said material.

13. The apparatus of claim 1, wherein said first end of said rocker arm is rigidly attached to a first end of an elongated pivot pin, said pivot pin being rotatably secured to said support structure, said actuation means comprising a crank or lever rigidly attached to a second end of said pivot pin, rotation of said crank causing said pivot pin and said rocker arm, and said curved guide means to rotate about said fixed pivot point, said rotation causing said curved guide means and said cutting means to advance or retract through said predetermined curved path.

14. The apparatus of claim 1, wherein said actuation means comprises a spring operationally secured to said support structure to urge rotation of said rocker arm.

15. The apparatus of claim 1, wherein said actuation means comprises a connecting rod pivotally secured to either said rocker arm or to said curved guide means, movement of said connecting rod causing said rocker arm, said curved guide means, and said cutting head to advance or retract through said predetermined curved path.

16. The apparatus of claim 15, wherein said connecting rod is secured to said rocker arm or to said curved guide means at a juncture between said rocker arm and said curved guide means.

17. The apparatus of claim 1, wherein said actuation means comprises a double parallel-crank mechanism.

18. The apparatus of claim 17, wherein said double parallel-crank mechanism comprises:

(a) said support structure;

(b) said rocker arm pivotally secured to said support structure at said fixed pivot point;

(c) a first crank system rotationally secured to said support structure;

(d) a second crank system rotationally secured to said support structure;

(e) at least one connecting rod having a first end, an intermediate point located along a length of said connecting rod, and a second end, said first end of said connecting rod being pivotally secured to said rocker arm, said first crank system being pivotally connected to said connecting rod at said intermediate point, said second end of said connecting rod being pivotally connected to said second crank system, said support structure, said rocker arm, said connecting rod, said first crank system, and said second crank system forming a plane parallelogram; and (f) means for rotating said first and said second crank systems, said rotating means being secured to at least said first crank system.

19. The apparatus of claim 18, wherein said means comprises at least one tension cord secured to said first crank system, longitudinal movement of said tension cord causing said first crank system to rotate which in turn causes said connecting rod to rotate said rocker arm and said second crank system.

20. The apparatus of claim 19, wherein said first crank system comprises at least one pulley, said first crank system and said pulley having a similar axis of rotation, said tension cord being passed around said pulley.

21. The apparatus of claim 18, further comprising a spring operationally secured to said support structure, said spring urging said first or said second crank system to rotate or to retract from an earlier rotation.

22. The apparatus of claim 19, further comprising a lever or trigger pivotally secured to said support structure, said tension cord being operationally secured to said lever in such a manner that movement of said lever causes said tension cord to move longitudinally and thereby rotate said first crank system.

23. The apparatus of claim 18, further comprising a meshed rack and pinion, said pinion being rigidly secured to said first crank system, said rack being slidably connected to said support structure, longitudinal movement of said rack causing said pinion and said first crank system to rotate which in turn causes said connecting rod to rotate said rocker arm and said second crank system.

24. The apparatus of claim 1, wherein said actuation means comprises a crossed-crank mechanism.

25. The apparatus of claim 24, wherein said crossed-crank mechanism comprises:
 (a) said support structure;
 (b) said rocker arm pivotally secured to said support structure at said fixed pivot point;
 (c) a crank system rotationally secured to said support structure;
 (d) at least one connecting rod having a first end, an intermediate point located along a length of said connecting rod, and a second end, said first end of said connecting rod being pivotally secured to said rocker arm, said second end of said connecting rod being pivotally secured to said crank system, said connecting serving as a lever between said rocker arm and said crank system;
 (e) a fulcrum secured to said support structure, said intermediate point being capable of being urged against said fulcrum, said fulcrum defining a rigid point of support about which said connecting rod pivots; and
 (f) means for rotating said crank system, said rotating means being secured to said crank system.

26. The apparatus of claim 25, wherein said intermediate point comprises a slide or pin, said fulcrum being defined by interior side walls of a groove, slot, or channel member formed within or secured to said support structure.

27. The apparatus of claim 25, wherein said rotating means comprises at least one tension cord secured to said crank system, longitudinal movement of said tension cord causing said crank system to rotate which in turn causes said connecting rod to pivot about said fulcrum and rotate said rocker.

28. The apparatus of claim 27, wherein said crank system comprises at least one pulley, said crank system and said pulley having a similar axis of rotation, said tension cord being passed around said pulley.

29. The apparatus of claim 25, further comprising a spring operationally secured to said support structure, said spring urging said crank system to rotate or to retract from an earlier rotation.

30. The apparatus of claim 27, further comprising a lever or trigger pivotally secured to said support structure, said tension cord being operationally secured to said lever in such a manner that movement of said lever causes said tension cord to move longitudinally and thereby rotate said crank system.

31. The apparatus of claim 1, wherein multiple said rocker arms, said curved guide means, said cutting means, and said actuation means are used in unison.

32. The apparatus of claim 31, wherein multiple said rocker arms, said curved guide means, said cutting means, and said actuation means are used within a single support structure.

33. The apparatus of claim 1, wherein said support structure permits said cutting means to have a wide range of orientations with respect to said material, said orientations being achieved by bending or contouring said support structure and said actuation means to orient said curved guide means and said cutting means at various angles with respect to said material.

* * * * *

UNITED STATES PATENT AND TRADEMARK OFFICE
CERTIFICATE OF CORRECTION

PATENT NO. : 5,002,546
DATED : March 26, 1991
INVENTOR(S) : J.W. Romano

It is certified that error appears in the above-identified patent and that said Letters Patent is hereby corrected as shown below:

| COLUMN | LINE | |
|---|---|---|
| 7 | 21 & 22 | "sideeleva-tional" should be --side-elevational-- |
| 9 | 24 | "crosssectional" should be --cross-sectional-- |
| 9 | 27 | "crosssectional" should be --cross-sectional-- |
| 10 | 40 | "crosssectional" should be --cross-sectional-- |
| 12 | 61 & 62 | "coppertung-sten" should be --copper-tungsten-- |
| 13 | 10 | "crosssectional" should be --cross-sectional-- |
| 22 (claim 9) | 66 (line 1) | after "said" insert --rotating-- |

Signed and Sealed this

Third Day of November, 1992

*Attest:*

DOUGLAS B. COMER

*Attesting Officer*     *Acting Commissioner of Patents and Trademarks*